US005863888A

United States Patent [19]
Dionne et al.

[11] Patent Number: 5,863,888
[45] Date of Patent: Jan. 26, 1999

[54] HUMAN BEK FIBROBLAST GROWTH FACTOR RECEPTOR

[75] Inventors: Craig A. Dionne, Blue Bell; Gregg B. Crumley, Philadelphia; Michael C. Jaye, Glenside; Joseph Schlessinger, Wayne, all of Pa.

[73] Assignee: Rhone-Poulenc Rorer Pharmaceuticals Inc., Collegeville, Pa.

[21] Appl. No.: 451,822

[22] Filed: May 26, 1995

Related U.S. Application Data

[63] Continuation of Ser. No. 323,430, Oct. 14, 1994, which is a continuation of Ser. No. 934,372, Aug. 21, 1992, abandoned, which is a continuation of Ser. No. 549,587, Jul. 6, 1990, abandoned.

[51] Int. Cl.$^6$ .................................................. C07K 14/705
[52] U.S. Cl. .............................. 514/2; 530/350; 530/395; 530/399; 435/691
[58] Field of Search ................................ 514/2; 435/69.1; 530/350, 395, 399

[56] References Cited

PUBLICATIONS

J. Biol. Chem. 260: 13860–13868, 1985, Neufeld Gospodarowicz, English Original.
J. Biol. Chem. 263: 14023–14029, 1988, Feige Baird English Original.
Biochem. Biophys. Res. Commun. 155: 583–590, 1988, Imamura Tokita Mitsui, English Original.
Molec. and Cell. Biol. 8: 5541–5544, 1988, Kornbluth Paulson Hanafusa, English Original.
Oncogene 3: 9–15, 1988, Ruta Howk Ricca, Drohan Zabelshansky et al., English Original.
J. Biol. Chem. 264: 18647–18653, 1989, Burrus Olwin, English Original.
Science 245: 57–60, 1989, Lee Johnson Cousens, Fried Williams, English Original.
Proc. Natl. Acad. Sci. USA 86: 5449–5453, 1989, Pasquale singer, English Original.
Proc. Natl. Acad. Sci. USA 86: 8722–8726, 1989, Ruta Burgess Givol, Epstein Neiger et al., English Original.
Nucleic Acids Res. 18: 1906, 1990, Isacchi Bergonzoni Sarmientos, English Original.
Science 248: 1410–1413, 1990, Kaner Baird Mansukhani, Basilico Summers et al., English Original.
Proc. Natl. Acad. Sci. USA 87: 1596–1600, 1990, Reid Wilks Bernard, English Original.
Cold Spring Harbor Laboratory, 1982, Maniatis et al., English Original.
Green Publishing Assoc. and Wiley Interscience, 1987, Ausubel, et al., eds., English Original.
Biochem. Biophys. Res. Commun. 169: 680–685, 1990, Itoh Terachi Ohta, Seo, English Original.
Molec. Cell. Biol. 11:4627–4634, Sep. 1991, Johnson Lu Chen, Werner Williams, English Original.
Growth Factors 5:115–127, 1991, Kiefer Baird Nguyen, George–Nascime Mason et al., English Original.
Molec. Cell. Biol. 11:5068–5078, 1993, Mohammadi Honegger Rotin, Fischer Bellot et al., English Original.
WO 91/00916, Jul. 6, 1990, Jan. 24, 1991, Williams Johnson Lee, English Original.
Sambrook et al., Molecular Cloning, A lab. Manual, Second Edition, vol. 3, pp. 16.2–16.30 and 71.2–17.28, 1989 Cold Spring Harbor Lab. Press, Cold Spring Harbor.
Duan et al., J. of Biol. Chem., 266, 413–418, 1991.

*Primary Examiner*—Sally P. Teng

[57] ABSTRACT

The complete cDNA cloning of two human genes previously designated flg and bek is disclosed. These genes encode for two similar but distinct surface receptors comprised of an extracellular domain with three immunoglobulin-like regions, a single transmembrane domain, and a cytoplasmic portion containing a tyrosine kinase domain with a typical kinase insert. The expression of these two cDNAs in transfected NIH-3T3 cells led to the biosynthesis of proteins of 150 kDa and 135 kDa for flg and bek respectively. Direct binding experiments with radiolabeled acidic FGF (aFGF), basic FGF (bFGF), or kFGF inhibition of binding with native growth factors, and Scatchard analysis of the binding data indicated that bek and flg bind aFGF, bFGF, or kFGF with dissociation constants of $(2–15)\times10^{-11}$M. The high affinity binding of three distinct growth factors to each of two different receptors represents a unique double redundancy without precedence among polypeptide growth factor/receptor interactions. The use of transformed host cells overexpressing flg or bek or biologically active fragments thereof for drug screening is disclosed.

9 Claims, 16 Drawing Sheets

| | | |
|---|---|---|
| FLG | MWSWKCLLFWAVLVTATLCTARPS------PTL-PEQAQPWGAPVEVESFLVHPGDLLQLRCRLRDD | 60 |
| BEK | V   GRFICLV VTM      SL    FSLVEDT  E  EPPTKYQISQP VYVAA  ES EV - LK | 66 |
| FLG | VQSINWLRDGVQLAESNRTRITGEEVEVQDSVPADSGLYACVTSSPSGSDTTYFSVNVSDALPSSED | 127 |
| BEK | AAV S TK   H GPN     VLI  YLQIKGAT  R      TA RTVD E W M  T -I  G | 132 |
| FLG | DDDDDDSSSEEKETDNTKPNRMPVAPYWTSPEKMEKKLHAVPAAKTVKFKCPSSGTPNPTLRWLKNG | 194 |
| BEK | E  --J--TDGA DFVSENSNNKR    NT    R      N    R  AG N M  M | 195 |
| FLG | KEFKPDHRIGGYKVRYATWSIIMDSVVPSDKGNYTCIVENEYGSINHTYQLDVVERSPHRPILQAGL | 261 |
| BEK | QE         NQH  L  E          V          H | 262 |
| FLG | PANKTVALGSNVEFMCKVYSDPQPHIQWLKHIEVNGSKIGPDNLPYVQILKTAGVNTTDKEMEVLHL | 328 |
| BEK | ASTVV GD   V        A     I  V K   Y  G  LKV A           I   YI | 329 |
| FLG | RNVSFEDAGEYTCLAGNSIGLSHHSAWLTVLEALEERPAVMTSPLYLEIIIYCTGAFLISCMVGSVI | 395 |
| BEK | T            I F       P PGREKEITA  D    A    I V    A    VT | 396 |
| FLG | VYKMKSGTKKSDFHSQMAVHKLAKSIPLRRQVTVSADSSASMNSGVLLVR-PSRLSS-SGTPMLAGV | 460 |
| BEK | LCR  NT      P  S P    T R       E  S    NTP  ITT     TAD | 463 |
| FLG | SEYELPEDPRWELPRDRLVLGKPLGEGCFGQVVLAEAIGLDKDKPNRVTKVAVKMLKSDATEKDLSD | 527 |
| BEK | K  F   K T          M  V I       KEAVT    D | 530 |
| FLG | LISEMEMMKMIGKHKNIINLLGACTQDGPLYVIVEYASKGNLREYLQARRPPGLEYCYNPSHNPEEQ | 594 |
| BEK | V                                    R     M  S DINRV | 597 |
| FLG | LSSKDLVSCAYQVARGMEYLASKKCIHRDLAARNVLVTEDNVMKIADFGLARDIHHIDYYKKTTNGR | 661 |
| BEK | MTF    T  L     Q            N          NN | 664 |
| FLG | LPVKWMAPEALFDRIYTHQSDVWSFGVLLWEIFTLGGSPYPGVPVEELFKLLKEGHRMDKPSNCTNE | 728 |
| BEK | V         M    I                    A | 730 |
| FLG | LYMMMRDCWHAVPSQRPTFKQLVEDLDRIVALTSNQEYLDLSMPLDQYSPSFPDTRSSTCSSGEDSV | 795 |
| BEK | LT  T E     Q    E      Y    -    D | 796 |
| FLG | FSHEPLPEEPCLPRHPAQLANGGLKRR | 822 |
| BEK | PD M Y    --QYPHI  SV T- | 821 |

FIG. 2A

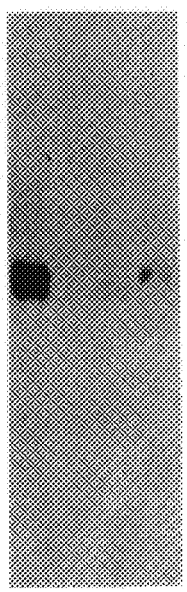 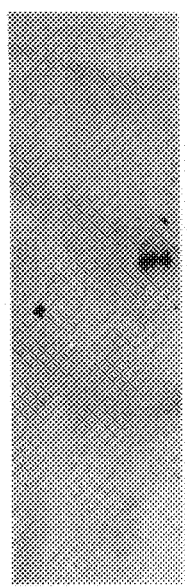
FIG. 3A   FIG. 3B
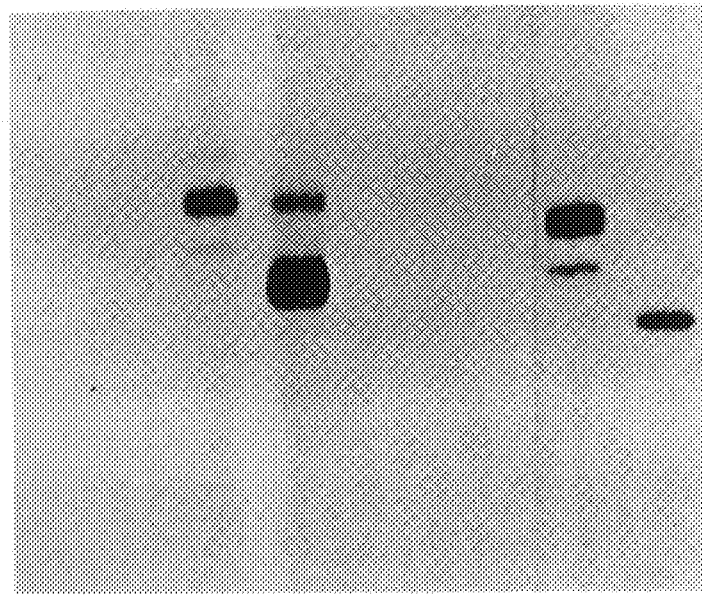
FIG. 4

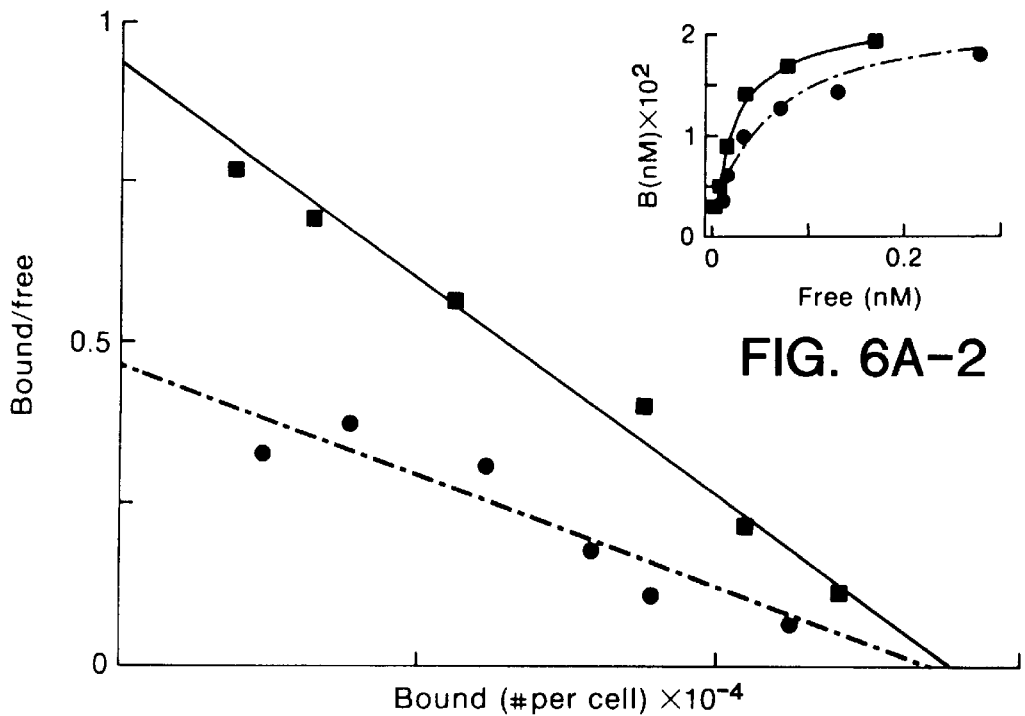
FIG. 6A-1
FIG. 6A-2
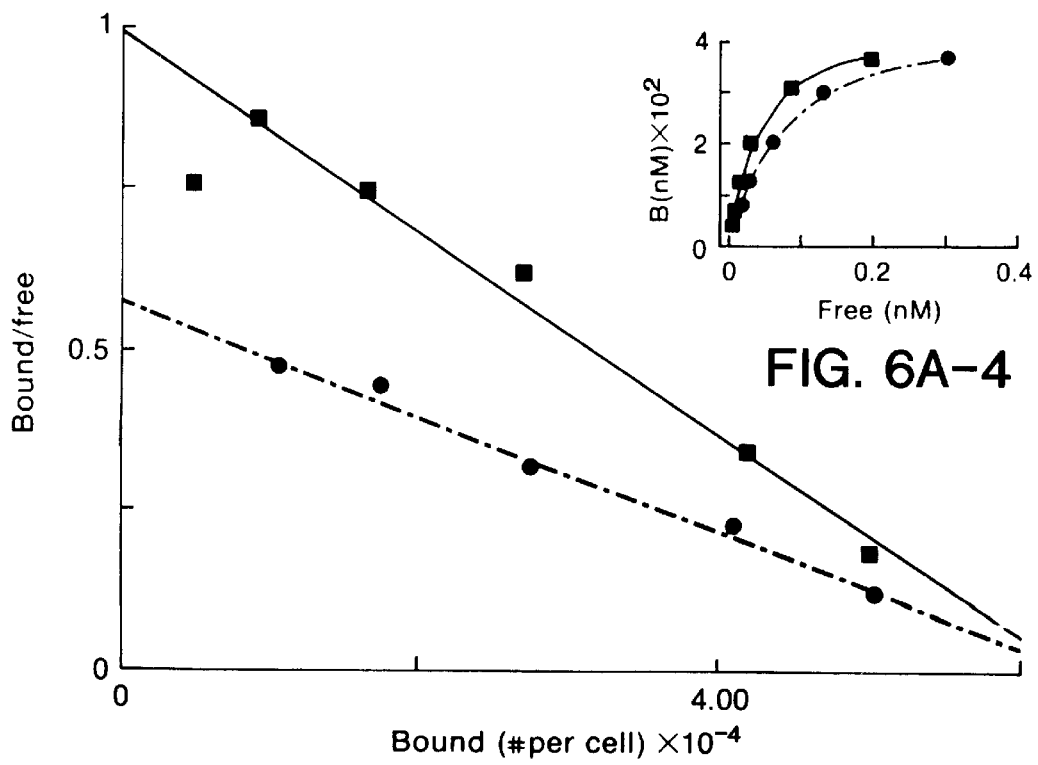
FIG. 6A-3
FIG. 6A-4

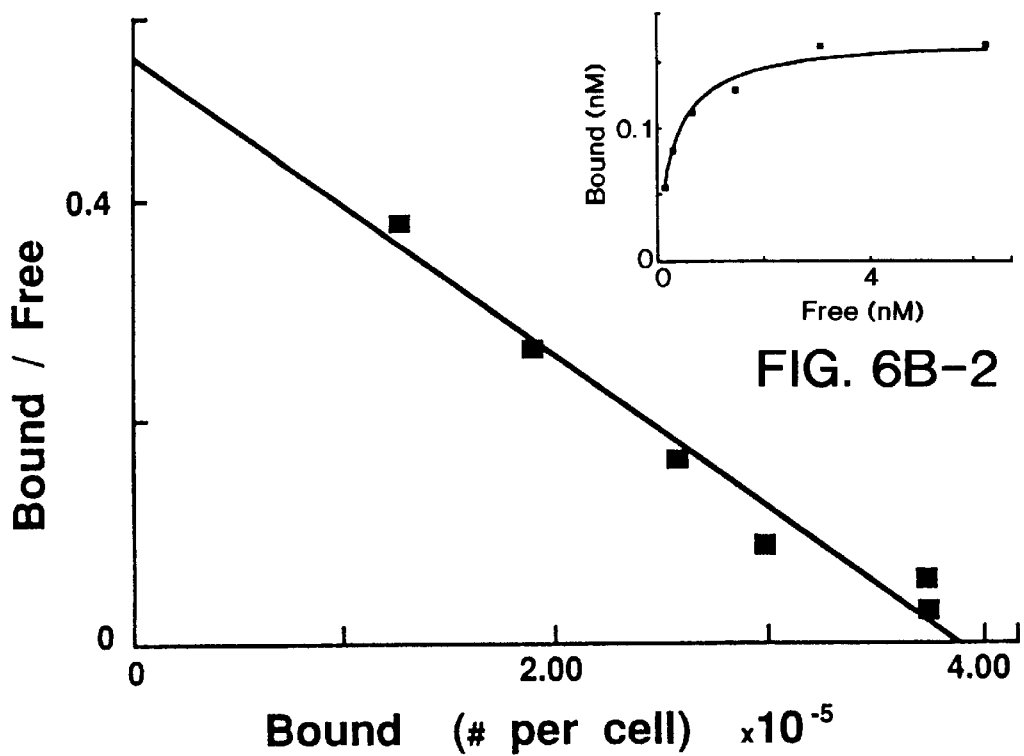
FIG. 6B-1
FIG. 6B-2
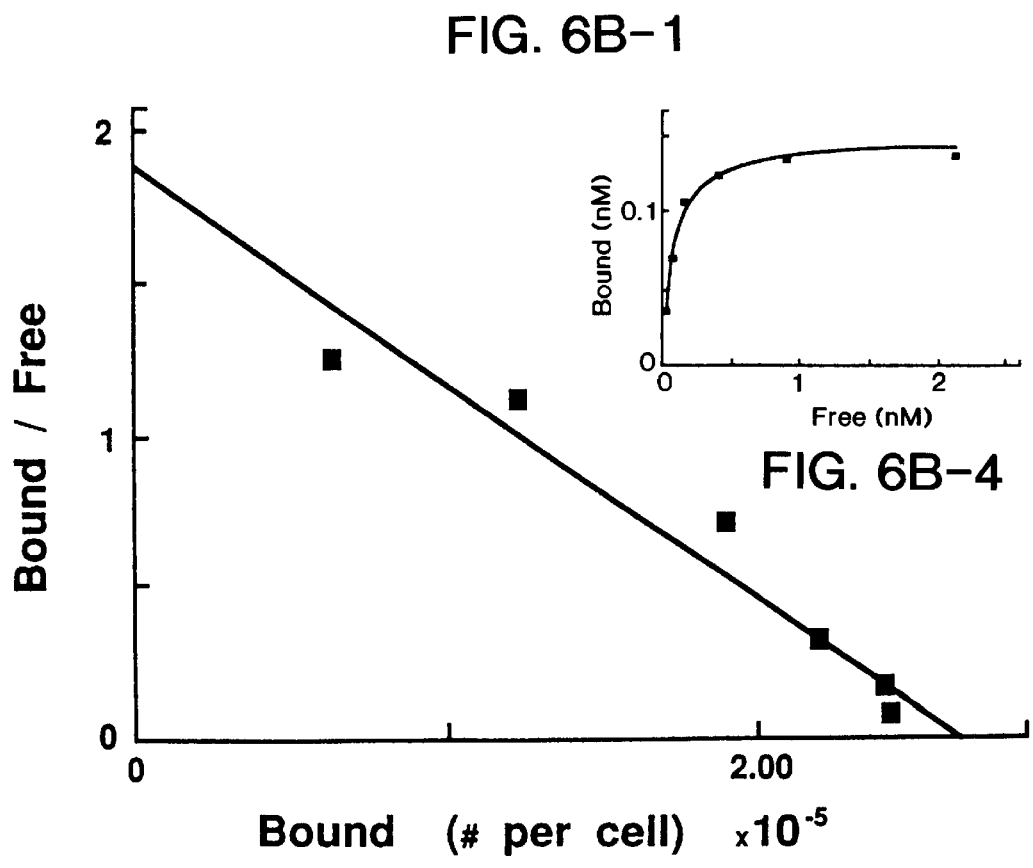
FIG. 6B-3
FIG. 6B-4

```
TCAGTTTGAA AAGGAGGATC GAGCTCACTC GTGGAGTATC CATGGAGATG TGGAGCCTTG         60

TCACCAACCT CTAACTGCAG AACTGGG ATG TGG AGC TGG AAG TGC CTC CTC           111
                              Met Trp Ser Trp Lys Cys Leu Leu
                               1                   5

TTC TGG GCT GTG CTG GTC ACA GCC ACA CTC TGC ACC GCT AGG CCG TCC         159
Phe Trp Ala Val Leu Val Thr Ala Thr Leu Cys Thr Ala Arg Pro Ser
     10                  15                  20

CCG ACC TTG CCT GAA CAA GCC CAG CCC TGG GGA GCC CCT GTG GAA GTG         207
Pro Thr Leu Pro Glu Gln Ala Gln Pro Trp Gly Ala Pro Val Glu Val
 25                  30                  35                  40

GAG TCC TTC CTG GTC CAC CCC GGT GAC CTG CTG CAG CTT CGC TGT CGG         255
Glu Ser Phe Leu Val His Pro Gly Asp Leu Leu Gln Leu Arg Cys Arg
                     45                  50                  55

CTG CGG GAC GAT GTG CAG AGC ATC AAC TGG CTG CGG GAC GGG GTG CAG         303
Leu Arg Asp Asp Val Gln Ser Ile Asn Trp Leu Arg Asp Gly Val Gln
                 60                  65                  70

CTG GCG GAA AGC AAC CGC ACC CGC ATC ACA GGG GAG GAG GTG GAG GTG         351
Leu Ala Glu Ser Asn Arg Thr Arg Ile Thr Gly Glu Glu Val Glu Val
             75                  80                  85

CAG GAC TCC GTG CCC GCA GAC TCC GGC CTC TAT GCT TGC GTA ACC AGC         399
Gln Asp Ser Val Pro Ala Asp Ser Gly Leu Tyr Ala Cys Val Thr Ser
         90                  95                 100

AGC CCC TCG GGC AGT GAC ACC ACC TAC TTC TCC GTC AAT GTT TCA GAT         447
Ser Pro Ser Gly Ser Asp Thr Thr Tyr Phe Ser Val Asn Val Ser Asp
105                 110                 115                 120

GCT CTC CCC TCC TCG GAG GAT GAT GAT GAT GAT GAT GAC TCC TCT TCA         495
Ala Leu Pro Ser Ser Glu Asp Asp Asp Asp Asp Asp Asp Ser Ser Ser
                125                 130                 135

GAG GAG AAA GAA ACA GAT AAC ACC AAA CCA AAC CGT ATG CCC GTA GCT         543
Glu Glu Lys Glu Thr Asp Asn Thr Lys Pro Asn Arg Met Pro Val Ala
            140                 145                 150

CCA TAT TGG ACA TCC CCA GAA AAG ATG GAA AAG AAA TTG CAT GCA GTG         591
Pro Tyr Trp Thr Ser Pro Glu Lys Met Glu Lys Lys Leu His Ala Val
        155                 160                 165

CCG GCT GCC AAG ACA GTG AAG TTC AAA TGC CCT TCC AGT GGG ACC CCA         639
Pro Ala Ala Lys Thr Val Lys Phe Lys Cys Pro Ser Ser Gly Thr Pro
170                 175                 180

AAC CCC ACA CTG CGC TGG TTG AAA AAT GGC AAA GAA TTC AAA CCT GAC         687
Asn Pro Thr Leu Arg Trp Leu Lys Asn Gly Lys Glu Phe Lys Pro Asp
185                 190                 195                 200

CAC AGA ATT GGA GGC TAC AAG GTC CGT TAT GCC ACC TGG AGC ATC ATA         735
His Arg Ile Gly Gly Tyr Lys Val Arg Tyr Ala Thr Trp Ser Ile Ile
                205                 210                 215
```

FIG. 7A

```
ATG GAC TCT GTG GTG CCC TCT GAC AAG GGC AAC TAC ACC TGC ATT GTG        783
Met Asp Ser Val Val Pro Ser Asp Lys Gly Asn Tyr Thr Cys Ile Val
        220                 225                 230

GAG AAT GAG TAC GGC AGC ATC AAC CAC ACA TAC CAG CTG GAT GTC GTG        831
Glu Asn Glu Tyr Gly Ser Ile Asn His Thr Tyr Gln Leu Asp Val Val
            235                 240                 245

GAG CGG TCC CCT CAC CGC CCC ATC CTG CAA GCA GGG TTG CCC GCC AAC        879
Glu Arg Ser Pro His Arg Pro Ile Leu Gln Ala Gly Leu Pro Ala Asn
        250                 255                 260

AAA ACA GTG GCC CTG GGT AGC AAC GTG GAG TTC ATG TGT AAG GTG TAC        927
Lys Thr Val Ala Leu Gly Ser Asn Val Glu Phe Met Cys Lys Val Tyr
265                 270                 275                 280

AGT GAC CCG CAG CCG CAC ATC CAG TGG CTA AAG CAC ATC GAG GTG AAT        975
Ser Asp Pro Gln Pro His Ile Gln Trp Leu Lys His Ile Glu Val Asn
                285                 290                 295

GGG AGC AAG ATT GGC CCA GAC AAC CTG CCT TAT GTC CAG ATC TTG AAG       1023
Gly Ser Lys Ile Gly Pro Asp Asn Leu Pro Tyr Val Gln Ile Leu Lys
            300                 305                 310

ACT GCT GGA GTT AAT ACC ACC GAC AAA GAG ATG GAG GTG CTT CAC TTA       1071
Thr Ala Gly Val Asn Thr Thr Asp Lys Glu Met Glu Val Leu His Leu
        315                 320                 325

AGA AAT GTC TCC TTT GAG GAC GCA GGG GAG TAT ACG TGC TTG GCG GGT       1119
Arg Asn Val Ser Phe Glu Asp Ala Gly Glu Tyr Thr Cys Leu Ala Gly
    330                 335                 340

AAC TCT ATC GGA CTC TCC CAT CAC TCT GCA TGG TTG ACC GTT CTG GAA       1167
Asn Ser Ile Gly Leu Ser His His Ser Ala Trp Leu Thr Val Leu Glu
345                 350                 355                 360

GCC CTG GAA GAG AGG CCG GCA GTG ATG ACC TCG CCC CTG TAC CTG GAG       1215
Ala Leu Glu Glu Arg Pro Ala Val Met Thr Ser Pro Leu Tyr Leu Glu
            365                 370                 375

ATC ATC ATC TAT TGC ACA GGG GCC TTC CTC ATC TCC TGC ATG GTG GGG       1263
Ile Ile Ile Tyr Cys Thr Gly Ala Phe Leu Ile Ser Cys Met Val Gly
        380                 385                 390

TCG GTC ATC GTC TAC AAG ATG AAG AGT GGT ACC AAG AAG AGT GAC TTC       1311
Ser Val Ile Val Tyr Lys Met Lys Ser Gly Thr Lys Lys Ser Asp Phe
    395                 400                 405

CAC AGC CAG ATG GCT GTG CAC AAG CTG GCC AAG AGC ATC CCT CTG CGC       1359
His Ser Gln Met Ala Val His Lys Leu Ala Lys Ser Ile Pro Leu Arg
        410                 415                 420

AGA CAG GTA ACA GTG TCT GCT GAC TCC AGT GCA TCC ATG AAC TCT GGG       1407
Arg Gln Val Thr Val Ser Ala Asp Ser Ser Ala Ser Met Asn Ser Gly
425                 430                 435                 440
```

FIG. 7B

| | | |
|---|---|---|
| GTT CTT CTG GTT CGG CCA TCA CGG CTC TCC TCC AGT GGG ACT CCC ATG | 1455 |
| Val Leu Leu Val Arg Pro Ser Arg Leu Ser Ser Ser Gly Thr Pro Met | |
| 445 450 455 | |
| CTA GCA GGG GTC TCT GAG TAT GAG CTT CCC GAA GAC CCT CGC TGG GAG | 1503 |
| Leu Ala Gly Val Ser Glu Tyr Glu Leu Pro Glu Asp Pro Arg Trp Glu | |
| 460 465 470 | |
| CTG CCT CGG GAC AGA CTG GTC TTA GGC AAA CCC CTG GGA GAG GGC TGC | 1551 |
| Leu Pro Arg Asp Arg Leu Val Leu Gly Lys Pro Leu Gly Glu Gly Cys | |
| 475 480 485 | |
| TTT GGG CAG GTG GTG TTG GCA GAG GCT ATC GGG CTG GAC AAG GAC AAA | 1599 |
| Phe Gly Gln Val Val Leu Ala Glu Ala Ile Gly Leu Asp Lys Asp Lys | |
| 490 495 500 | |
| CCC AAC CGT GTG ACC AAA GTG GCT GTG AAG ATG TTG AAG TCG GAC GCA | 1647 |
| Pro Asn Arg Val Thr Lys Val Ala Val Lys Met Leu Lys Ser Asp Ala | |
| 505 510 515 520 | |
| ACA GAG AAA GAC TTG TCA GAC CTG ATC TCA GAA ATG GAG ATG ATG AAG | 1695 |
| Thr Glu Lys Asp Leu Ser Asp Leu Ile Ser Glu Met Glu Met Met Lys | |
| 525 530 535 | |
| ATG ATC GGG AAG CAT AAG AAT ATC ATC AAC CTG CTG GGG GCC TGC ACG | 1743 |
| Met Ile Gly Lys His Lys Asn Ile Ile Asn Leu Leu Gly Ala Cys Thr | |
| 540 545 550 | |
| CAG GAT GGT CCC TTG TAT GTC ATC GTG GAG TAT GCC TCC AAG GGC AAC | 1791 |
| Gln Asp Gly Pro Leu Tyr Val Ile Val Glu Tyr Ala Ser Lys Gly Asn | |
| 555 560 565 | |
| CTG CGG GAG TAC CTG CAG GCC CGG AGG CCC CCA GGG CTG GAA TAC TGC | 1839 |
| Leu Arg Glu Tyr Leu Gln Ala Arg Arg Pro Pro Gly Leu Glu Tyr Cys | |
| 570 575 580 | |
| TAC AAC CCC AGC CAC AAC CCA GAG GAG CAG CTC TCC TCC AAG GAC CTG | 1887 |
| Tyr Asn Pro Ser His Asn Pro Glu Glu Gln Leu Ser Ser Lys Asp Leu | |
| 585 590 595 600 | |
| GTG TCC TGC GCC TAC CAG GTG GCC CGA GGC ATG GAG TAT CTG GCC TCC | 1935 |
| Val Ser Cys Ala Tyr Gln Val Ala Arg Gly Met Glu Tyr Leu Ala Ser | |
| 605 610 615 | |
| AAG AAG TGC ATA CAC CGA GAC CTG GCA GCC AGG AAT GTC CTG GTG ACA | 1983 |
| Lys Lys Cys Ile His Arg Asp Leu Ala Ala Arg Asn Val Leu Val Thr | |
| 620 625 630 | |
| GAG GAC AAT GTG ATG AAG ATA GCA GAC TTT GGC CTC GCA CGG GAC ATT | 2031 |
| Glu Asp Asn Val Met Lys Ile Ala Asp Phe Gly Leu Ala Arg Asp Ile | |
| 635 640 645 | |
| CAC CAC ATC GAC TAC TAT AAA AAG ACA ACC AAC GGC CGA CTG CCT GTG | 2079 |
| His His Ile Asp Tyr Tyr Lys Lys Thr Thr Asn Gly Arg Leu Pro Val | |
| 650 655 660 | |
| AAG TGG ATG GCA CCC GAG GCA TTA TTT GAC CGG ATC TAC ACC CAC CAG | 2127 |

FIG. 7C

```
Lys Trp Met Ala Pro Glu Ala Leu Phe Asp Arg Ile Tyr Thr His Gln
665             670              675              680

AGT GAT GTG TGG TCT TTC GGG GTG CTC CTG TGG GAG ATC TTC ACT CTG         2175
Ser Asp Val Trp Ser Phe Gly Val Leu Leu Trp Glu Ile Phe Thr Leu
                685              690              695

GGC GGC TCC CCA TAC CCC GGT GTG CCT GTG GAG GAA CTT TTC AAG CTG         2223
Gly Gly Ser Pro Tyr Pro Gly Val Pro Val Glu Glu Leu Phe Lys Leu
                700              705              710

CTG AAG GAG GGT CAC CGC ATG GAC AAG CCC AGT AAC TGC ACC AAC GAG         2271
Leu Lys Glu Gly His Arg Met Asp Lys Pro Ser Asn Cys Thr Asn Glu
        715              720              725

CTG TAC ATG ATG ATG CGG GAC TGC TGG CAT GCA GTG CCC TCA CAG AGA         2319
Leu Tyr Met Met Met Arg Asp Cys Trp His Ala Val Pro Ser Gln Arg
        730              735              740

CCC ACC TTC AAG CAG CTG GTG GAA GAC CTG GAC CGC ATC GTG GCC TTG         2367
Pro Thr Phe Lys Gln Leu Val Glu Asp Leu Asp Arg Ile Val Ala Leu
745              750              755              760

ACC TCC AAC CAG GAG TAC CTG GAC CTG TCC ATG CCC CTG GAC CAG TAC         2415
Thr Ser Asn Gln Glu Tyr Leu Asp Leu Ser Met Pro Leu Asp Gln Tyr
                765              770              775

TCC CCC AGC TTT CCC GAC ACC CGG AGC TCT ACG TGC TCC TCA GGG GAG         2463
Ser Pro Ser Phe Pro Asp Thr Arg Ser Ser Thr Cys Ser Ser Gly Glu
                780              785              790

GAT TCC GTC TTC TCT CAT GAG CCG CTG CCC GAG GAG CCC TGC CTG CCC         2511
Asp Ser Val Phe Ser His Glu Pro Leu Pro Glu Glu Pro Cys Leu Pro
        795              800              805

CGA CAC CCA GCC CAG CTT GCC AAT GGC GGA CTC AAA CGC CGC TGA             2556
Arg His Pro Ala Gln Leu Ala Asn Gly Gly Leu Lys Arg Arg *
        810              815              820

CTGCCACCCA CACGCCCTCC CCAGACTCCA CCGTCAGCTG TAACCCTCAC CCACAGCCCC       2616

TGCCTGGGCC CACCACCTGT CCGTCCCTGT CCCCTTTCCT GCTGGG                      2662
```

FIG. 7D

| | |
|---|---:|
| CCCCAGGTCG CGGAGGAGCG TTGCCATTCA AGTGACTGCA GCAGCAGCGG CACCGCTCGG | 60 |
| TTCCTGAGCC CACCGCAGCT GAAGGCATTG CGCGTAGTCC ATGCCCGTAG AGGAAGTGTG | 120 |
| CAGATGGGAT TAACGTCCAC ATGGAGATAT GGAAGAGGAC CGGGGATTGG TACCGTAACC | 180 |

```
ATG GTC AGC TGG GGT CGT TTC ATC TGC CTG GTC GTG GTC ACC ATG GCA      228
Met Val Ser Trp Gly Arg Phe Ile Cys Leu Val Val Val Thr Met Ala
    825                 830                 835

ACC TTG TCC CTG GCC CGG CCC TCC TTC AGT TTA GTT GAG GAT ACC ACA      276
Thr Leu Ser Leu Ala Arg Pro Ser Phe Ser Leu Val Glu Asp Thr Thr
840                 845                 850                 855

TTA GAG CCA GAA GAG CCA CCA ACC AAA TAC CAA ATC TCT CAA CCA GAA      324
Leu Glu Pro Glu Glu Pro Pro Thr Lys Tyr Gln Ile Ser Gln Pro Glu
                860                 865                 870

GTG TAC GTG GCT GCA CCA GGG GAG TCG CTA GAG GTG CGC TGC CTG TTG      372
Val Tyr Val Ala Ala Pro Gly Glu Ser Leu Glu Val Arg Cys Leu Leu
                    875                 880                 885

AAA GAT GCC GCC GTG ATC AGT TGG ACT AAG GAT GGG GTG CAC TTG GGG      420
Lys Asp Ala Ala Val Ile Ser Trp Thr Lys Asp Gly Val His Leu Gly
            890                 895                 900

CCC AAC AAT AGG ACA GTG CTT ATT GGG GAG TAC TTG CAG ATA AAG GGC      468
Pro Asn Asn Arg Thr Val Leu Ile Gly Glu Tyr Leu Gln Ile Lys Gly
            905                 910                 915

GCC ACG CCT AGA GAC TCC GGC CTC TAT GCT TGT ACT GCC AGT AGG ACT      516
Ala Thr Pro Arg Asp Ser Gly Leu Tyr Ala Cys Thr Ala Ser Arg Thr
920                 925                 930                 935

GTA GAC AGT GAA ACT TGG TAC TTC ATG GTG AAT GTC ACA GAT GCC ATC      564
Val Asp Ser Glu Thr Trp Tyr Phe Met Val Asn Val Thr Asp Ala Ile
                940                 945                 950

TCA TCC GGA GAT GAT GAG GAT GAC ACC GAT GGT GCG GAA GAT TTT GTC      612
Ser Ser Gly Asp Asp Glu Asp Asp Thr Asp Gly Ala Glu Asp Phe Val
            955                 960                 965

AGT GAG AAC AGT AAC AAC AAG AGA GCA CCA TAC TGG ACC AAC ACA GAA      660
Ser Glu Asn Ser Asn Asn Lys Arg Ala Pro Tyr Trp Thr Asn Thr Glu
        970                 975                 980

AAG ATG GAA AAG CGG CTC CAT GCT GTG CCT GCG GCC AAC ACT GTC AAG      708
Lys Met Glu Lys Arg Leu His Ala Val Pro Ala Ala Asn Thr Val Lys
985                 990                 995

TTT CGC TGC CCA GCC GGG GGG AAC CCA ATG CCA ACC ATG CGG TGG CTG      756
Phe Arg Cys Pro Ala Gly Gly Asn Pro Met Pro Thr Met Arg Trp Leu
1000                1005                1010                1015

AAA AAC GGG AAG GAG TTT AAG CAG GAG CAT CGC ATT GGA GGC TAC AAG      804
Lys Asn Gly Lys Glu Phe Lys Gln Glu His Arg Ile Gly Gly Tyr Lys
                1020                1025                1030
```

FIG. 8A

```
GTA CGA AAC CAG CAC TGG AGC CTC ATT ATG GAA AGT GTG GTC CCA TCT                852
Val Arg Asn Gln His Trp Ser Leu Ile Met Glu Ser Val Val Pro Ser
        1035                1040                1045

GAC AAG GGA AAT TAT ACC TGT GTG GTG GAG AAT GAA TAC GGG TCC ATC                900
Asp Lys Gly Asn Tyr Thr Cys Val Val Glu Asn Glu Tyr Gly Ser Ile
        1050                1055                1060

AAT CAC ACG TAC CAC CTG GAT GTT GTG GAG CGA TCG CCT CAC CGG CCC                948
Asn His Thr Tyr His Leu Asp Val Val Glu Arg Ser Pro His Arg Pro
        1065                1070                1075

ATC CTC CAA GCC GGA CTG CCG GCA AAT GCC TCC ACA GTG GTC GGA GGA                996
Ile Leu Gln Ala Gly Leu Pro Ala Asn Ala Ser Thr Val Val Gly Gly
1080                1085                1090                1095

GAC GTA GAG TTT GTC TGC AAG GTT TAC AGT GAT GCC CAG CCC CAC ATC               1044
Asp Val Glu Phe Val Cys Lys Val Tyr Ser Asp Ala Gln Pro His Ile
                1100                1105                1110

CAG TGG ATC AAG CAC GTG GAA AAG AAC GGC AGT AAA TAC GGG CCC GAC               1092
Gln Trp Ile Lys His Val Glu Lys Asn Gly Ser Lys Tyr Gly Pro Asp
        1115                1120                1125

GGG CTG CCC TAC CTC AAG GTT CTC AAG GCC GCC GGT GTT AAC ACC ACG               1140
Gly Leu Pro Tyr Leu Lys Val Leu Lys Ala Ala Gly Val Asn Thr Thr
        1130                1135                1140

GAC AAA GAG ATT GAG GTT CTC TAT ATT CGG AAT GTA ACT TTT GAG GAC               1188
Asp Lys Glu Ile Glu Val Leu Tyr Ile Arg Asn Val Thr Phe Glu Asp
        1145                1150                1155

GCT GGG GAA TAT ACG TGC TTG GCG GGT AAT TCT ATT GGG ATA TCC TTT               1236
Ala Gly Glu Tyr Thr Cys Leu Ala Gly Asn Ser Ile Gly Ile Ser Phe
1160                1165                1170                1175

CAC TCT GCA TGG TTG ACA GTT CTG CCA GCG CCT GGA AGA GAA AAG GAG               1284
His Ser Ala Trp Leu Thr Val Leu Pro Ala Pro Gly Arg Glu Lys Glu
                1180                1185                1190

ATT ACA GCT TCC CCA GAC TAC CTG GAG ATA GCC ATT TAC TGC ATA GGG               1332
Ile Thr Ala Ser Pro Asp Tyr Leu Glu Ile Ala Ile Tyr Cys Ile Gly
        1195                1200                1205

GTC TTC TTA ATC GCC TGT ATG GTG GTA ACA GTC ATC CTG TGC CGA ATG               1380
Val Phe Leu Ile Ala Cys Met Val Val Thr Val Ile Leu Cys Arg Met
        1210                1215                1220

AAG AAC ACG ACC AAG AAG CCA GAC TTC AGC AGC CAG CCG GCT GTG CAC               1428
Lys Asn Thr Thr Lys Lys Pro Asp Phe Ser Ser Gln Pro Ala Val His
        1225                1230                1235

AAG CTG ACC AAA CGT ATC CCC CTG CGG AGA CAG GTA ACA GTT TCG GCT               1476
Lys Leu Thr Lys Arg Ile Pro Leu Arg Arg Gln Val Thr Val Ser Ala
1240                1245                1250                1255
```

FIG. 8B

```
GAG TCC AGC TCC TCC ATG AAC TCC AAC ACC CCG CTG GTG AGG ATA ACA    1524
Glu Ser Ser Ser Ser Met Asn Ser Asn Thr Pro Leu Val Arg Ile Thr
                    1260            1265            1270

ACA CGC CTC TCT TCA ACG GCA GAC ACC CCC ATG CTG GCA GGG GTC TCC    1572
Thr Arg Leu Ser Ser Thr Ala Asp Thr Pro Met Leu Ala Gly Val Ser
                1275            1280            1285

GAG TAT GAA CTT CCA GAG GAC CCA AAA TGG GAG TTT CCA AGA GAT AAG    1620
Glu Tyr Glu Leu Pro Glu Asp Pro Lys Trp Glu Phe Pro Arg Asp Lys
            1290            1295            1300

CTG ACA CTG GGC AAG CCC CTG GGA GAA GGT TGC TTT GGG CAA GTG GTC    1668
Leu Thr Leu Gly Lys Pro Leu Gly Glu Gly Cys Phe Gly Gln Val Val
            1305            1310            1315

ATG GCG GAA GCA GTG GGA ATT GAC AAA GAC AAG CCC AAG GAG GCG GTC    1716
Met Ala Glu Ala Val Gly Ile Asp Lys Asp Lys Pro Lys Glu Ala Val
1320            1325            1330            1335

ACC GTG GCC GTG AAG ATG TTG AAA GAT GAT GCC ACA GAG AAA GAC CTT    1764
Thr Val Ala Val Lys Met Leu Lys Asp Asp Ala Thr Glu Lys Asp Leu
                1340            1345            1350

TCT GAT CTG GTG TCA GAG ATG GAG ATG ATG AAG ATG ATT GGG AAA CAC    1812
Ser Asp Leu Val Ser Glu Met Glu Met Met Lys Met Ile Gly Lys His
            1355            1360            1365

AAG AAT ATC ATA AAT CTT CTT GGA GCC TGC ACA CAG GAT GGG CCT CTC    1860
Lys Asn Ile Ile Asn Leu Leu Gly Ala Cys Thr Gln Asp Gly Pro Leu
            1370            1375            1380

TAT GTC ATA GTT GAG TAT GCC TCT AAA GGC AAC CTC CGA GAA TAC CTC    1908
Tyr Val Ile Val Glu Tyr Ala Ser Lys Gly Asn Leu Arg Glu Tyr Leu
            1385            1390            1395

CGA GCC CGG AGG CCA CCC GGG ATG GAG TAC TCC TAT GAC ATT AAC CGT    1956
Arg Ala Arg Arg Pro Pro Gly Met Glu Tyr Ser Tyr Asp Ile Asn Arg
1400            1405            1410            1415

GTT CCT GAG GAG CAG ATG ACC TTC AAG GAC TTG GTG TCA TGC ACC TAC    2004
Val Pro Glu Glu Gln Met Thr Phe Lys Asp Leu Val Ser Cys Thr Tyr
                1420            1425            1430

CAG CTG GCC AGA GGC ATG GAG TAC TTG GCT TCC CAA AAA TGT ATT CAT    2052
Gln Leu Ala Arg Gly Met Glu Tyr Leu Ala Ser Gln Lys Cys Ile His
            1435            1440            1445

CGA GAT TTA GCA GCC AGA AAT GTT TTG GTA ACA GAA AAC AAT GTG ATG    2100
Arg Asp Leu Ala Ala Arg Asn Val Leu Val Thr Glu Asn Asn Val Met
            1450            1455            1460

AAA ATA GCA GAC TTT GGA CTC GCC AGA GAT ATC AAC AAT ATA GAC TAT    2148
Lys Ile Ala Asp Phe Gly Leu Ala Arg Asp Ile Asn Asn Ile Asp Tyr
            1465            1470            1475

TAC AAA AAG ACC ACC AAT GGG CGG CTT CCA GTC AAG TGG ATG GCT CCA    2196
```

FIG. 8C

```
                Tyr Lys Lys Thr Thr Asn Gly Arg Leu Pro Val Lys Trp Met Ala Pro
                1480            1485            1490            1495

GAA GCC CTG TTT GAT AGA GTA TAC ACT CAT CAG AGT GAT GTC TGG TCC          2244
Glu Ala Leu Phe Asp Arg Val Tyr Thr His Gln Ser Asp Val Trp Ser
                1500            1505            1510

TTC GGG GTG TTA ATG TGG GAG ATC TTC ACT TTA GGG GGC TCG CCC TAC          2292
Phe Gly Val Leu Met Trp Glu Ile Phe Thr Leu Gly Gly Ser Pro Tyr
                1515            1520            1525

CCA GGG ATT CCC GTG GAG GAA CTT TTT AAG CTG CTG AAG GAA GGA CAC          2340
Pro Gly Ile Pro Val Glu Glu Leu Phe Lys Leu Leu Lys Glu Gly His
                1530            1535            1540

AGA ATG GAT AAG CCA GCC AAC TGC ACC AAC GAA CTG TAC ATG ATG ATG          2388
Arg Met Asp Lys Pro Ala Asn Cys Thr Asn Glu Leu Tyr Met Met Met
                1545            1550            1555

AGG GAC TGT TGG CAT GCA GTG CCC TCC CAG AGA CCA ACG TTC AAG CAG          2436
Arg Asp Cys Trp His Ala Val Pro Ser Gln Arg Pro Thr Phe Lys Gln
1560            1565            1570            1575

TTG GTA GAA GAC TTG GAT CGA ATT CTC ACT CTC ACA ACC AAT GAG GAA          2484
Leu Val Glu Asp Leu Asp Arg Ile Leu Thr Leu Thr Thr Asn Glu Glu
                1580            1585            1590

TAC TTG GAC CTC AGC CAA CCT CTC GAA CAG TAT TCA CCT AGT TAC CCT          2532
Tyr Leu Asp Leu Ser Gln Pro Leu Glu Gln Tyr Ser Pro Ser Tyr Pro
                1595            1600            1605

GAC ACA AGA AGT TCT TGT TCT TCA GGA GAT GAT TCT GTT TTT TCT CCA          2580
Asp Thr Arg Ser Ser Cys Ser Ser Gly Asp Asp Ser Val Phe Ser Pro
                1610            1615            1620

GAC CCC ATG CCT TAC GAA CCA TGC CTT CCT CAG TAT CCA CAC ATA AAC          2628
Asp Pro Met Pro Tyr Glu Pro Cys Leu Pro Gln Tyr Pro His Ile Asn
                1625            1630            1635

GGC AGT GTT AAA ACA TGA ATGACTGTGT CTGCCTGTCC CCAAACAGGA                 2676
Gly Ser Val Lys Thr *
                1640            1645

CAGCACTGGG AACCTAGCTA CACTGAGCAG GGAGACCATG CCTCCCAGAG CTTGTTGTCT        2736

CCACTTGTAT ATATGGATCA GAGGAGTAAA TAATTGGAAA AGTAATCAGC ATATGTGTAA        2796

AGATTTATAC AGTTGAAAAC TTGTAATCTT CCCCAGGAGG AGAAGAAGGT TTCTGGAGCA        2856

GTGGACTGCC ACAAGCCACC ATGTAACCCC TCTCACCTGC CGTGCGTACT GGCTGTGGAC        2916

CAGTAGGACT CAAGGTGGAC GTGCGTTCTG CCTTCCTTGT TAATTTTGTA ATAATTGGAG        2976

AAGATTTATG TCAGCACACA CTTACAGAGC ACAAATGCAG TATATAGGTG CTGGATGTAT        3036

GTAAATATAT TCAAATTATG TATAAATATA TATTATATAT TTACAAGGAG TTATTTTTTG        3096
```

FIG. 8D

```
TATTGATTTT AAATGGATGT CCCAATGCAC CTAGAAAATT GGTCTCTCTT TTTTTAATAG    3156

CTATTTGCTA AATGCTGTTC TTACACATAA TTTCTTAATT TTCACCGAGC AGAGGTGGAA    3216

AAATACTTTT GCTTTCAGGG AAAATGGTAT AACGTTAATT TATTAATAAA TTGGTAATAT    3276

ACAAAACAAT TAATCATTTA TAGTTTTTTT TGTAATTTAA GTGGCATTTC TATGCAGGCA    3336

GCACAGCAGA CTAGTTAATC TATTGCTTGG ACTTAACTAG TTATCAGATC CTTTGAAAAG    3396

AGAATATTTA CAATATATGA                                                3416
```

FIG. 8E

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

G C A T G C G C G C      G G C C G C G G A G      G C C                                                       2 3

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single (D) TOPOLOGY: linear (ii) MOLECULE TYPE: cDNA (xi) SEQUENCE DESCRIPTION: SEQ ID NO:2:

GCATGCGCGC GGCCGCGGAG GCCCCCCCCC CCCCC    35

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ACATCCAGCT GGTATGTGTG    20

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TACGGTCGAC CGTACTCATT CTCCACAATG CA    32

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCCATTTTTC AACCAGCGC    19

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGGGTTTGGG GTCCCACTGG AA    22

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TGACACCAGA CCAACTGGTA ATGG                                                                    24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TAATGGTAGC GACCGGCGCT CAGC                                                                    24

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TCATGTTTTA ACACTGCCGT TTATGTGTGG ATA                                                          33

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GGAATTCAAG CTTCTAGACC ACCATGGTCA GCTGGGGTCG TTTCA                                              45

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TCCTATTGTT GGGCCCCAAG TGCA                                                                    24

( 2 ) INFORMATION FOR SEQ ID NO:12:

( i ) SEQUENCE CHARACTERISTICS:
        ( A ) LENGTH: 822 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
    Met  Trp  Ser  Trp  Lys  Cys  Leu  Leu  Phe  Trp  Ala  Val  Leu  Val  Thr  Ala
    1              5                        10                       15

Thr  Leu  Cys  Thr  Ala  Arg  Pro  Ser  Pro  Thr  Leu  Pro  Glu  Gln  Ala  Gln
```

|  |  | 20 |  |  |  | 25 |  |  |  | 30 |  |  |
|--|--|----|--|--|--|----|--|--|--|----|--|--|

Pro Trp Gly Ala Pro Val Glu Val Glu Ser Phe Leu Val His Pro Gly
         35                40                  45

Asp Leu Leu Gln Leu Arg Cys Arg Leu Arg Asp Asp Val Gln Ser Ile
 50                  55                  60

Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
             85                  90                  95

Gly Leu Tyr Ala Cys Val Thr Ser Ser Pro Ser Gly Ser Asp Thr Thr
             100               105               110

Tyr Phe Ser Val Asn Val Ser Asp Ala Leu Pro Ser Ser Glu Asp Asp
         115               120               125

Asp Asp Asp Asp Asp Ser Ser Ser Glu Glu Lys Glu Thr Asp Asn Thr
     130               135               140

Lys Pro Asn Arg Met Pro Val Ala Pro Tyr Trp Thr Ser Pro Glu Lys
145               150               155               160

Met Glu Lys Lys Leu His Ala Val Pro Ala Ala Lys Thr Val Lys Phe
                 165               170               175

Lys Cys Pro Ser Ser Gly Thr Pro Asn Pro Thr Leu Arg Trp Leu Lys
             180               185               190

Asn Gly Lys Glu Phe Lys Pro Asp His Arg Ile Gly Gly Tyr Lys Val
         195               200               205

Arg Tyr Ala Thr Trp Ser Ile Ile Met Asp Ser Val Pro Ser Asp
     210               215               220

Lys Gly Asn Tyr Thr Cys Ile Val Glu Asn Glu Tyr Gly Ser Ile Asn
225               230               235               240

His Thr Tyr Gln Leu Asp Val Val Glu Arg Ser Pro His Arg Pro Ile
                 245               250               255

Leu Gln Ala Gly Leu Pro Ala Asn Lys Thr Val Ala Leu Gly Ser Asn
             260               265               270

Val Glu Phe Met Cys Lys Val Tyr Ser Asp Pro Gln Pro His Ile Gln
         275               280               285

Trp Leu Lys His Ile Glu Val Asn Gly Ser Lys Ile Gly Pro Asp Asn
     290               295               300

Leu Pro Tyr Val Gln Ile Leu Lys Thr Ala Gly Val Asn Thr Thr Asp
305               310               315               320

Lys Glu Met Glu Val Leu His Leu Arg Asn Val Ser Phe Glu Asp Ala
             325               330               335

Gly Glu Tyr Thr Cys Leu Ala Gly Asn Ser Ile Gly Leu Ser His His
         340               345               350

Ser Ala Trp Leu Thr Val Leu Glu Ala Leu Glu Glu Arg Pro Ala Val
     355               360               365

Met Thr Ser Pro Leu Tyr Leu Glu Ile Ile Ile Tyr Cys Thr Gly Ala
     370               375               380

Phe Leu Ile Ser Cys Met Val Gly Ser Val Ile Val Tyr Lys Met Lys
385               390               395               400

Ser Gly Thr Lys Lys Ser Asp Phe His Ser Gln Met Ala Val His Lys
             405               410               415

Leu Ala Lys Ser Ile Pro Leu Arg Arg Gln Val Thr Val Ser Ala Asp
             420               425               430

Ser Ser Ala Ser Met Asn Ser Gly Val Leu Leu Val Arg Pro Ser Arg
         435               440               445

-continued

| | | | | | | | | | | | | | | |
|---|---|---|---|---|---|---|---|---|---|---|---|---|---|---|
| Leu | Ser | Ser | Ser | Gly | Thr | Pro | Met | Leu | Ala | Gly | Val | Ser | Glu | Tyr | Glu |
| | 450 | | | | 455 | | | | | 460 | | | | | |
| Leu | Pro | Glu | Asp | Pro | Arg | Trp | Glu | Leu | Pro | Arg | Asp | Arg | Leu | Val | Leu |
| 465 | | | | | 470 | | | | | 475 | | | | | 480 |
| Gly | Lys | Pro | Leu | Gly | Glu | Gly | Cys | Phe | Gln | Val | Val | Leu | Ala | Glu |
| | | | | 485 | | | | | 490 | | | | | 495 |
| Ala | Ile | Gly | Leu | Asp | Lys | Asp | Lys | Pro | Asn | Arg | Val | Thr | Lys | Val | Ala |
| | | | 500 | | | | | 505 | | | | | 510 | | |
| Val | Lys | Met | Leu | Lys | Ser | Asp | Ala | Thr | Glu | Lys | Asp | Leu | Ser | Asp | Leu |
| | | 515 | | | | | 520 | | | | | 525 | | | |
| Ile | Ser | Glu | Met | Glu | Met | Met | Lys | Met | Ile | Gly | Lys | His | Lys | Asn | Ile |
| | 530 | | | | | 535 | | | | | 540 | | | | |
| Ile | Asn | Leu | Leu | Gly | Ala | Cys | Thr | Gln | Asp | Gly | Pro | Leu | Tyr | Val | Ile |
| 545 | | | | | 550 | | | | | 555 | | | | | 560 |
| Val | Glu | Tyr | Ala | Ser | Lys | Gly | Asn | Leu | Arg | Glu | Tyr | Leu | Gln | Ala | Arg |
| | | | | 565 | | | | | 570 | | | | | 575 | |
| Arg | Pro | Pro | Gly | Leu | Glu | Tyr | Cys | Tyr | Asn | Pro | Ser | His | Asn | Pro | Glu |
| | | | 580 | | | | | 585 | | | | | 590 | | |
| Glu | Gln | Leu | Ser | Ser | Lys | Asp | Leu | Val | Ser | Cys | Ala | Tyr | Gln | Val | Ala |
| | | | 595 | | | | | 600 | | | | | 605 | | |
| Arg | Gly | Met | Glu | Tyr | Leu | Ala | Ser | Lys | Lys | Cys | Ile | His | Arg | Asp | Leu |
| | | 610 | | | | | 615 | | | | | 620 | | | |
| Ala | Ala | Arg | Asn | Val | Leu | Val | Thr | Glu | Asp | Asn | Val | Met | Lys | Ile | Ala |
| 625 | | | | | 630 | | | | | 635 | | | | | 640 |
| Asp | Phe | Gly | Leu | Ala | Arg | Asp | Ile | His | His | Ile | Asp | Tyr | Tyr | Lys | Lys |
| | | | | 645 | | | | | 650 | | | | | 655 | |
| Thr | Thr | Asn | Gly | Arg | Leu | Pro | Val | Lys | Trp | Met | Ala | Pro | Glu | Ala | Leu |
| | | | 660 | | | | | 665 | | | | | 670 | | |
| Phe | Asp | Arg | Ile | Tyr | Thr | His | Gln | Ser | Asp | Val | Trp | Ser | Phe | Gly | Val |
| | | 675 | | | | | 680 | | | | | 685 | | | |
| Leu | Leu | Trp | Glu | Ile | Phe | Thr | Leu | Gly | Gly | Ser | Pro | Tyr | Pro | Gly | Val |
| | 690 | | | | | 695 | | | | | 700 | | | | |
| Pro | Val | Glu | Glu | Leu | Phe | Lys | Leu | Leu | Lys | Glu | Gly | His | Arg | Met | Asp |
| 705 | | | | | 710 | | | | | 715 | | | | | 720 |
| Lys | Pro | Ser | Asn | Cys | Thr | Asn | Glu | Leu | Tyr | Met | Met | Met | Arg | Asp | Cys |
| | | | | 725 | | | | | 730 | | | | | 735 | |
| Trp | His | Ala | Val | Pro | Ser | Gln | Arg | Pro | Thr | Phe | Lys | Gln | Leu | Val | Glu |
| | | | 740 | | | | | 745 | | | | | 750 | | |
| Asp | Leu | Asp | Arg | Ile | Val | Ala | Leu | Thr | Ser | Asn | Gln | Glu | Tyr | Leu | Asp |
| | | 755 | | | | | 760 | | | | | 765 | | | |
| Leu | Ser | Met | Pro | Leu | Asp | Gln | Tyr | Ser | Pro | Ser | Phe | Pro | Asp | Thr | Arg |
| | 770 | | | | | 775 | | | | | 780 | | | | |
| Ser | Ser | Thr | Cys | Ser | Ser | Gly | Glu | Asp | Ser | Val | Phe | Ser | His | Glu | Pro |
| 785 | | | | | 790 | | | | | 795 | | | | | 800 |
| Leu | Pro | Glu | Glu | Pro | Cys | Leu | Pro | Arg | His | Pro | Ala | Gln | Leu | Ala | Asn |
| | | | | 805 | | | | | 810 | | | | | 815 | |
| Gly | Gly | Leu | Lys | Arg | Arg | | | | | | | | | | |
| | | | 820 | | | | | | | | | | | | |

( 2 ) INFORMATION FOR SEQ ID NO:13:

( i ) SEQUENCE CHARACTERISTICS:
        ( A ) LENGTH: 821 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

| Met | Val | Ser | Trp | Gly | Arg | Phe | Ile | Cys | Leu | Val | Val | Thr | Met | Ala |
|---|---|---|---|---|---|---|---|---|---|---|---|---|---|---|
| 1 | | | | 5 | | | | | 10 | | | | | 15 |

| Thr | Leu | Ser | Leu | Ala | Arg | Pro | Ser | Phe | Ser | Leu | Val | Glu | Asp | Thr | Thr |
|---|---|---|---|---|---|---|---|---|---|---|---|---|---|---|---|
| | | | 20 | | | | 25 | | | | | 30 | | | |

| Leu | Glu | Pro | Glu | Glu | Pro | Pro | Thr | Lys | Tyr | Gln | Ile | Ser | Gln | Pro | Glu |
|---|---|---|---|---|---|---|---|---|---|---|---|---|---|---|---|
| | | 35 | | | | | 40 | | | | 45 | | | | |

| Val | Tyr | Val | Ala | Ala | Pro | Gly | Glu | Ser | Leu | Glu | Val | Arg | Cys | Leu | Leu |
|---|---|---|---|---|---|---|---|---|---|---|---|---|---|---|---|
| | 50 | | | | | 55 | | | | | 60 | | | | |

| Lys | Asp | Ala | Ala | Val | Ile | Ser | Trp | Thr | Lys | Asp | Gly | Val | His | Leu | Gly |
|---|---|---|---|---|---|---|---|---|---|---|---|---|---|---|---|
| 65 | | | | | 70 | | | | | 75 | | | | | 80 |

| Pro | Asn | Asn | Arg | Thr | Val | Leu | Ile | Gly | Glu | Tyr | Leu | Gln | Ile | Lys | Gly |
|---|---|---|---|---|---|---|---|---|---|---|---|---|---|---|---|
| | | | | 85 | | | | | 90 | | | | | 95 | |

| Ala | Thr | Pro | Arg | Asp | Ser | Gly | Leu | Tyr | Ala | Cys | Thr | Ala | Ser | Arg | Thr |
|---|---|---|---|---|---|---|---|---|---|---|---|---|---|---|---|
| | | | 100 | | | | | 105 | | | | | 110 | | |

| Val | Asp | Ser | Glu | Thr | Trp | Tyr | Phe | Met | Val | Asn | Val | Thr | Asp | Ala | Ile |
|---|---|---|---|---|---|---|---|---|---|---|---|---|---|---|---|
| | | 115 | | | | | 120 | | | | | 125 | | | |

| Ser | Ser | Gly | Asp | Asp | Glu | Asp | Asp | Thr | Asp | Gly | Ala | Glu | Asp | Phe | Val |
|---|---|---|---|---|---|---|---|---|---|---|---|---|---|---|---|
| | 130 | | | | | 135 | | | | | 140 | | | | |

| Ser | Glu | Asn | Ser | Asn | Asn | Lys | Arg | Ala | Pro | Tyr | Trp | Thr | Asn | Thr | Glu |
|---|---|---|---|---|---|---|---|---|---|---|---|---|---|---|---|
| 145 | | | | | 150 | | | | | 155 | | | | | 160 |

| Lys | Met | Glu | Lys | Arg | Leu | His | Ala | Val | Pro | Ala | Ala | Asn | Thr | Val | Lys |
|---|---|---|---|---|---|---|---|---|---|---|---|---|---|---|---|
| | | | | 165 | | | | | 170 | | | | | 175 | |

| Phe | Arg | Cys | Pro | Ala | Gly | Gly | Asn | Pro | Met | Pro | Thr | Met | Arg | Trp | Leu |
|---|---|---|---|---|---|---|---|---|---|---|---|---|---|---|---|
| | | | 180 | | | | | 185 | | | | | 190 | | |

| Lys | Asn | Gly | Lys | Glu | Phe | Lys | Gln | Glu | His | Arg | Ile | Gly | Gly | Tyr | Lys |
|---|---|---|---|---|---|---|---|---|---|---|---|---|---|---|---|
| | | 195 | | | | | 200 | | | | | 205 | | | |

| Val | Arg | Asn | Gln | His | Trp | Ser | Leu | Ile | Met | Glu | Ser | Val | Val | Pro | Ser |
|---|---|---|---|---|---|---|---|---|---|---|---|---|---|---|---|
| | 210 | | | | | 215 | | | | | 220 | | | | |

| Asp | Lys | Gly | Asn | Tyr | Thr | Cys | Val | Val | Glu | Asn | Glu | Tyr | Gly | Ser | Ile |
|---|---|---|---|---|---|---|---|---|---|---|---|---|---|---|---|
| 225 | | | | | 230 | | | | | 235 | | | | | 240 |

| Asn | His | Thr | Tyr | His | Leu | Asp | Val | Val | Glu | Arg | Ser | Pro | His | Arg | Pro |
|---|---|---|---|---|---|---|---|---|---|---|---|---|---|---|---|
| | | | | 245 | | | | | 250 | | | | | 255 | |

| Ile | Leu | Gln | Ala | Gly | Leu | Pro | Ala | Asn | Ala | Ser | Thr | Val | Val | Gly | Gly |
|---|---|---|---|---|---|---|---|---|---|---|---|---|---|---|---|
| | | | 260 | | | | | 265 | | | | | 270 | | |

| Asp | Val | Glu | Phe | Val | Cys | Lys | Val | Tyr | Ser | Asp | Ala | Gln | Pro | His | Ile |
|---|---|---|---|---|---|---|---|---|---|---|---|---|---|---|---|
| | | 275 | | | | | 280 | | | | | 285 | | | |

| Gln | Trp | Ile | Lys | His | Val | Glu | Lys | Asn | Gly | Ser | Lys | Tyr | Gly | Pro | Asp |
|---|---|---|---|---|---|---|---|---|---|---|---|---|---|---|---|
| | 290 | | | | | 295 | | | | | 300 | | | | |

| Gly | Leu | Pro | Tyr | Leu | Lys | Val | Leu | Lys | Ala | Ala | Gly | Val | Asn | Thr | Thr |
|---|---|---|---|---|---|---|---|---|---|---|---|---|---|---|---|
| 305 | | | | | 310 | | | | | 315 | | | | | 320 |

| Asp | Lys | Glu | Ile | Glu | Val | Leu | Tyr | Ile | Arg | Asn | Val | Thr | Phe | Glu | Asp |
|---|---|---|---|---|---|---|---|---|---|---|---|---|---|---|---|
| | | | | 325 | | | | | 330 | | | | | 335 | |

| Ala | Gly | Glu | Tyr | Thr | Cys | Leu | Ala | Gly | Asn | Ser | Ile | Gly | Ile | Ser | Phe |
|---|---|---|---|---|---|---|---|---|---|---|---|---|---|---|---|
| | | | 340 | | | | | 345 | | | | | 350 | | |

| His | Ser | Ala | Trp | Leu | Thr | Val | Leu | Pro | Ala | Pro | Gly | Arg | Glu | Lys | Glu |
|---|---|---|---|---|---|---|---|---|---|---|---|---|---|---|---|
| | | 355 | | | | | 360 | | | | | 365 | | | |

| Ile | Thr | Ala | Ser | Pro | Asp | Tyr | Leu | Glu | Ile | Ala | Ile | Tyr | Cys | Ile | Gly |
|---|---|---|---|---|---|---|---|---|---|---|---|---|---|---|---|
| | 370 | | | | | 375 | | | | | 380 | | | | |

| Val | Phe | Leu | Ile | Ala | Cys | Met | Val | Val | Thr | Val | Ile | Leu | Cys | Arg | Met |
|---|---|---|---|---|---|---|---|---|---|---|---|---|---|---|---|
| 385 | | | | | 390 | | | | | 395 | | | | | 400 |

```
Lys Asn Thr Thr Lys Lys Pro Asp Phe Ser Ser Gln Pro Ala Val His
            405             410                 415
Lys Leu Thr Lys Arg Ile Pro Leu Arg Arg Gln Val Thr Val Ser Ala
            420             425                 430
Glu Ser Ser Ser Ser Met Asn Ser Asn Thr Pro Leu Arg Ile Thr
        435             440                 445
Thr Arg Leu Ser Ser Thr Ala Asp Thr Pro Met Leu Ala Gly Val Ser
    450             455                 460
Glu Tyr Glu Leu Pro Glu Asp Pro Lys Trp Glu Phe Pro Arg Asp Lys
465             470              475                     480
Leu Thr Leu Gly Lys Pro Leu Gly Glu Gly Cys Phe Gly Gln Val Val
                485             490                 495
Met Ala Glu Ala Val Gly Ile Asp Lys Asp Lys Pro Lys Glu Ala Val
            500             505                 510
Thr Val Ala Val Lys Met Leu Lys Asp Asp Ala Thr Glu Lys Asp Leu
            515             520                 525
Ser Asp Leu Val Ser Glu Met Glu Met Met Lys Met Ile Gly Lys His
    530             535                 540
Lys Asn Ile Ile Asn Leu Leu Gly Ala Cys Thr Gln Asp Gly Pro Leu
545                 550                 555                 560
Tyr Val Ile Val Glu Tyr Ala Ser Lys Gly Asn Leu Arg Glu Tyr Leu
                565             570                 575
Arg Ala Arg Arg Pro Pro Gly Met Glu Tyr Ser Tyr Asp Ile Asn Arg
            580             585                 590
Val Pro Glu Glu Gln Met Thr Phe Lys Asp Leu Val Ser Cys Thr Tyr
            595             600                 605
Gln Leu Ala Arg Gly Met Glu Tyr Leu Ala Ser Gln Lys Cys Ile His
    610             615                 620
Arg Asp Leu Ala Ala Arg Asn Val Leu Val Thr Glu Asn Asn Val Met
625             630                 635                 640
Lys Ile Ala Asp Phe Gly Leu Ala Arg Asp Ile Asn Asn Ile Asp Tyr
            645             650                 655
Tyr Lys Lys Thr Thr Asn Gly Arg Leu Pro Val Lys Trp Met Ala Pro
            660             665                 670
Glu Ala Leu Phe Asp Arg Val Tyr Thr His Gln Ser Asp Val Trp Ser
        675             680                 685
Phe Gly Val Leu Met Trp Glu Ile Phe Thr Leu Gly Gly Ser Pro Tyr
    690             695                 700
Pro Gly Ile Pro Val Glu Glu Leu Phe Lys Leu Leu Lys Glu Gly His
705             710                 715                 720
Arg Met Asp Lys Pro Ala Asn Cys Thr Asn Glu Leu Tyr Met Met Met
            725             730                 735
Arg Asp Cys Trp His Ala Val Pro Ser Gln Arg Pro Thr Phe Lys Gln
            740             745                 750
Leu Val Glu Asp Leu Asp Arg Ile Leu Thr Leu Thr Thr Asn Glu Glu
        755             760                 765
Tyr Leu Asp Leu Ser Gln Pro Leu Glu Gln Tyr Ser Pro Ser Tyr Pro
    770             775                 780
Asp Thr Arg Ser Ser Cys Ser Ser Gly Asp Asp Ser Val Phe Ser Pro
785             790                 795                 800
Asp Pro Met Pro Tyr Glu Pro Cys Leu Pro Gln Tyr Pro His Ile Asn
            805             810                 815
Gly Ser Val Lys Thr
            820
```

( 2 ) INFORMATION FOR SEQ ID NO:14:

( i ) SEQUENCE CHARACTERISTICS:
        ( A ) LENGTH: 2662 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
TCAGTTTGAA  AAGGAGGATC  GAGCTCACTC  GTGGAGTATC  CATGGAGATG  TGGAGCCTTG    60
TCACCAACCT  CTAACTGCAG  AACTGGGATG  TGGAGCTGGA  AGTGCCTCCT  CTTCTGGGCT   120
GTGCTGGTCA  CAGCCACACT  CTGCACCGCT  AGGCCGTCCC  CGACCTTGCC  TGAACAAGCC   180
CAGCCCTGGG  GAGCCCCTGT  GGAAGTGGAG  TCCTTCCTGG  TCCACCCCGG  TGACCTGCTG   240
CAGCTTCGCT  GTCGGCTGCG  GGACGATGTG  CAGAGCATCA  ACTGGCTGCG  GGACGGGGTG   300
CAGCTGGCGG  AAAGCAACCG  CACCCGCATC  ACAGGGGAGG  AGGTGGAGGT  GCAGGACTCC   360
GTGCCCGCAG  ACTCCGGCCT  CTATGCTTGC  GTAACCAGCA  GCCCCTCGGG  CAGTGACACC   420
ACCTACTTCT  CCGTCAATGT  TTCAGATGCT  CTCCCCTCCT  CGGAGGATGA  TGATGATGAT   480
GATGACTCCT  CTTCAGAGGA  GAAAGAAACA  GATAACACCA  AACCAAACCG  TATGCCCGTA   540
GCTCCATATT  GGACATCCCC  AGAAAAGATG  GAAAAGAAAT  TGCATGCAGT  GCCGGCTGCC   600
AAGACAGTGA  AGTTCAAATG  CCCTTCCAGT  GGGACCCCAA  ACCCCACACT  GCGCTGGTTG   660
AAAAATGGCA  AAGAATTCAA  ACCTGACCAC  AGAATTGGAG  GCTACAAGGT  CCGTTATGCC   720
ACCTGGAGCA  TCATAATGGA  CTCTGTGGTG  CCCTCTGACA  AGGGCAACTA  CACCTGCATT   780
GTGGAGAATG  AGTACGGCAG  CATCAACCAC  ACATACCAGC  TGGATGTCGT  GGAGCGGTCC   840
CCTCACCGCC  CCATCCTGCA  AGCAGGGTTG  CCCGCCAACA  AAACAGTGGC  CCTGGGTAGC   900
AACGTGGAGT  TCATGTGTAA  GGTGTACAGT  GACCCGCAGC  CGCACATCCA  GTGGCTAAAG   960
CACATCGAGG  TGAATGGGAG  CAAGATTGGC  CCAGACAACC  TGCCTTATGT  CCAGATCTTG  1020
AAGACTGCTG  GAGTTAATAC  CACCGACAAA  GAGATGGAGG  TGCTTCACTT  AAGAAATGTC  1080
TCCTTTGAGG  ACGCAGGGGA  GTATACGTGC  TTGGCGGGTA  ACTCTATCGG  ACTCTCCCAT  1140
CACTCTGCAT  GGTTGACCGT  TCTGGAAGCC  CTGGAAGAGA  GGCCGGCAGT  GATGACCTCG  1200
CCCCTGTACC  TGGAGATCAT  CATCTATTGC  ACAGGGGCCT  TCCTCATCTC  CTGCATGGTG  1260
GGGTCGGTCA  TCGTCTACAA  GATGAAGAGT  GGTACCAAGA  AGAGTGACTT  CCACAGCCAG  1320
ATGGCTGTGC  ACAAGCTGGC  CAAGAGCATC  CCTCTGCGCA  GACAGGTAAC  AGTGTCTGCT  1380
GACTCCAGTG  CATCCATGAA  CTCTGGGGTT  CTTCTGGTTC  GGCCATCACG  GCTCTCCTCC  1440
AGTGGGACTC  CCATGCTAGC  AGGGGTCTCT  GAGTATGAGC  TTCCCGAAGA  CCCTCGCTGG  1500
GAGCTGCCTC  GGGACAGACT  GGTCTTAGGC  AAACCCCTGG  GAGAGGGCTG  CTTTGGGCAG  1560
GTGGTGTTGG  CAGAGGCTAT  CGGGCTGGAC  AAGGACAAAC  CAACCGTGT   GACCAAAGTG  1620
GCTGTGAAGA  TGTTGAAGTC  GGACGCAACA  GAGAAAGACT  TGTCAGACCT  GATCTCAGAA  1680
ATGGAGATGA  TGAAGATGAT  CGGGAAGCAT  AAGAATATCA  TCAACCTGCT  GGGGGCCTGC  1740
ACGCAGGATG  GTCCCTTGTA  TGTCATCGTG  GAGTATGCCT  CCAAGGGCAA  CCTGCGGGAG  1800
TACCTGCAGG  CCCGGAGGCC  CCCAGGGCTG  GAATACTGCT  ACAACCCCAG  CCACAACCCA  1860
GAGGAGCAGC  TCTCCTCCAA  GGACCTGGTG  TCCTGCGCCT  ACCAGGTGGC  CCGAGGCATG  1920
GAGTATCTGG  CCTCCAAGAA  GTGCATACAC  CGAGACCTGG  CAGCCAGGAA  TGTCCTGGTG  1980
```

-continued

| | | | | | | |
|---|---|---|---|---|---|---|
| ACAGAGGACA | ATGTGATGAA | GATAGCAGAC | TTTGGCCTCG | CACGGGACAT | TCACCACATC | 2040 |
| GACTACTATA | AAAAGACAAC | CAACGGCCGA | CTGCCTGTGA | AGTGGATGGC | ACCCGAGGCA | 2100 |
| TTATTTGACC | GGATCTACAC | CCACCAGAGT | GATGTGTGGT | CTTTCGGGGT | GCTCCTGTGG | 2160 |
| GAGATCTTCA | CTCTGGGCGG | CTCCCCATAC | CCCGGTGTGC | CTGTGGAGGA | ACTTTTCAAG | 2220 |
| CTGCTGAAGG | AGGGTCACCG | CATGGACAAG | CCCAGTAACT | GCACCAACGA | GCTGTACATG | 2280 |
| ATGATGCGGG | ACTGCTGGCA | TGCAGTGCCC | TCACAGAGAC | CCACCTTCAA | GCAGCTGGTG | 2340 |
| GAAGACCTGG | ACCGCATCGT | GGCCTTGACC | TCCAACCAGG | AGTACCTGGA | CCTGTCCATG | 2400 |
| CCCCTGGACC | AGTACTCCCC | CAGCTTTCCC | GACACCCGGA | GCTCTACGTG | CTCCTCAGGG | 2460 |
| GAGGATTCCG | TCTTCTCTCA | TGAGCCGCTG | CCCGAGGAGC | CCTGCCTGCC | CCGACACCCA | 2520 |
| GCCCAGCTTG | CCAATGGCGG | ACTCAAACGC | CGCTGACTGC | CACCCACACG | CCCTCCCCAG | 2580 |
| ACTCCACCGT | CAGCTGTAAC | CCTCACCCAC | AGCCCCTGCC | TGGGCCCACC | ACCTGTCCGT | 2640 |
| CCCTGTCCCC | TTTCCTGCTG | GG | | | | 2662 |

(2) INFORMATION FOR SEQ ID NO:15:

(i) SEQUENCE CHARACTERISTICS:
        (A) LENGTH: 3416 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

| | | | | | | |
|---|---|---|---|---|---|---|
| CCCCAGGTCG | CGGAGGAGCG | TTGCCATTCA | AGTGACTGCA | GCAGCAGCGG | CACCGCTCGG | 60 |
| TTCCTGAGCC | CACCGCAGCT | GAAGGCATTG | CGCGTAGTCC | ATGCCCGTAG | AGGAAGTGTG | 120 |
| CAGATGGGAT | TAACGTCCAC | ATGGAGATAT | GGAAGAGGAC | CGGGGATTGG | TACCGTAACC | 180 |
| ATGGTCAGCT | GGGGTCGTTT | CATCTGCCTG | GTCGTGGTCA | CCATGGCAAC | CTTGTCCCTG | 240 |
| GCCCGGCCCT | CCTTCAGTTT | AGTTGAGGAT | ACCACATTAG | AGCCAGAAGA | GCCACCAACC | 300 |
| AAATACCAAA | TCTCTCAACC | AGAAGTGTAC | GTGGCTGCAC | CAGGGGAGTC | GCTAGAGGTG | 360 |
| CGCTGCCTGT | TGAAAGATGC | CGCCGTGATC | AGTTGGACTA | AGGATGGGGT | GCACTTGGGG | 420 |
| CCCAACAATA | GGACAGTGCT | TATTGGGGAG | TACTTGCAGA | TAAAGGGCGC | CACGCCTAGA | 480 |
| GACTCCGGCC | TCTATGCTTG | TACTGCCAGT | AGGACTGTAG | ACAGTGAAAC | TTGGTACTTC | 540 |
| ATGGTGAATG | TCACAGATGC | CATCTCATCC | GGAGATGATG | AGGATGACAC | CGATGGTGCG | 600 |
| GAAGATTTTG | TCAGTGAGAA | CAGTAACAAC | AAGAGAGCAC | CATACTGGAC | CAACACAGAA | 660 |
| AAGATGGAAA | AGCGGCTCCA | TGCTGTGCCT | GCGGCCAACA | CTGTCAAGTT | CGCTGCCCA | 720 |
| GCCGGGGGGA | ACCCAATGCC | AACCATGCGG | TGGCTGAAAA | ACGGGAAGGA | GTTTAAGCAG | 780 |
| GAGCATCGCA | TTGGAGGCTA | CAAGGTACGA | AACCAGCACT | GGAGCCTCAT | TATGGAAAGT | 840 |
| GTGGTCCCAT | CTGACAAGGG | AAATTATACC | TGTGTGGTGG | AGAATGAATA | CGGGTCCATC | 900 |
| AATCACACGT | ACCACCTGGA | TGTTGTGGAG | CGATCGCCTC | ACCGGCCCAT | CCTCCAAGCC | 960 |
| GGACTGCCGG | CAAATGCCTC | CACAGTGGTC | GGAGGAGACG | TAGAGTTTGT | CTGCAAGGTT | 1020 |
| TACAGTGATG | CCCAGCCCCA | CATCCAGTGG | ATCAAGCACG | TGGAAAAGAA | CGGCAGTAAA | 1080 |
| TACGGGCCCG | ACGGGCTGCC | CTACCTCAAG | GTTCTCAAGG | CCGCCGGTGT | TAACACCACG | 1140 |
| GACAAAGAGA | TTGAGGTTCT | CTATATTCGG | AATGTAACTT | TTGAGGACGC | TGGGGAATAT | 1200 |
| ACGTGCTTGG | CGGGTAATTC | TATTGGGATA | TCCTTTCACT | CTGCATGGTT | GACAGTTCTG | 1260 |
| CCAGCGCCTG | GAAGAGAAAA | GGAGATTACA | GCTTCCCCAG | ACTACCTGGA | GATAGCCATT | 1320 |

-continued

```
TACTGCATAG GGGTCTTCTT AATCGCCTGT ATGGTGGTAA CAGTCATCCT GTGCCGAATG    1380

AAGAACACGA CCAAGAAGCC AGACTTCAGC AGCCAGCCGG CTGTGCACAA GCTGACCAAA    1440

CGTATCCCCC TGCGGAGACA GGTAACAGTT TCGGCTGAGT CCAGCTCCTC CATGAACTCC    1500

AACACCCCGC TGGTGAGGAT AACAACACGC CTCTCTTCAA CGGCAGACAC CCCCATGCTG    1560

GCAGGGGTCT CCGAGTATGA ACTTCCAGAG GACCCAAAAT GGGAGTTTCC AAGAGATAAG    1620

CTGACACTGG GCAAGCCCCT GGGAGAAGGT TGCTTTGGGC AAGTGGTCAT GGCGGAAGCA    1680

GTGGGAATTG ACAAAGACAA GCCCAAGGAG GCGGTCACCG TGGCCGTGAA GATGTTGAAA    1740

GATGATGCCA CAGAGAAAGA CCTTTCTGAT CTGGTGTCAG AGATGGAGAT GATGAAGATG    1800

ATTGGGAAAC ACAAGAATAT CATAAATCTT CTTGGAGCCT GCACACAGGA TGGGCCTCTC    1860

TATGTCATAG TTGAGTATGC CTCTAAAGGC AACCTCCGAG AATACCTCCG AGCCCGGAGG    1920

CCACCCGGGA TGGAGTACTC CTATGACATT AACCGTGTTC CTGAGGAGCA GATGACCTTC    1980

AAGGACTTGG TGTCATGCAC CTACCAGCTG GCCAGAGGCA TGGAGTACTT GGCTTCCCAA    2040

AAATGTATTC ATCGAGATTT AGCAGCCAGA AATGTTTTGG TAACAGAAAA CAATGTGATG    2100

AAAATAGCAG ACTTTGGACT CGCCAGAGAT ATCAACAATA TAGACTATTA CAAAAAGACC    2160

ACCAATGGGC GGCTTCCAGT CAAGTGGATG GCTCCAGAAG CCCTGTTTGA TAGAGTATAC    2220

ACTCATCAGA GTGATGTCTG GTCCTTCGGG GTGTTAATGT GGGAGATCTT CACTTTAGGG    2280

GGCTCGCCCT ACCCAGGGAT TCCCGTGGAG GAACTTTTTA AGCTGCTGAA GGAAGGACAC    2340

AGAATGGATA AGCCAGCCAA CTGCACCAAC GAACTGTACA TGATGATGAG GGACTGTTGG    2400

CATGCAGTGC CCTCCCAGAG ACCAACGTTC AAGCAGTTGG TAGAAGACTT GGATCGAATT    2460

CTCACTCTCA CAACCAATGA GGAATACTTG GACCTCAGCC AACCTCTCGA ACAGTATTCA    2520

CCTAGTTACC CTGACACAAG AAGTTCTTGT TCTTCAGGAG ATGATTCTGT TTTTTCTCCA    2580

GACCCCATGC CTTACGAACC ATGCCTTCCT CAGTATCCAC ACATAAACGG CAGTGTTAAA    2640

ACATGAATGA CTGTGTCTGC CTGTCCCCAA ACAGGACAGC ACTGGGAACC TAGCTACACT    2700

GAGCAGGGAG ACCATGCCTC CCAGAGCTTG TTGTCTCCAC TTGTATATAT GGATCAGAGG    2760

AGTAAATAAT TGGAAAAGTA ATCAGCATAT GTGTAAAGAT TTATACAGTT GAAAACTTGT    2820

AATCTTCCCC AGGAGGAGAA GAAGGTTTCT GGAGCAGTGG ACTGCCACAA GCCACCATGT    2880

AACCCCTCTC ACCTGCCGTG CGTACTGGCT GTGGACCAGT AGGACTCAAG GTGGACGTGC    2940

GTTCTGCCTT CCTTGTTAAT TTTGTAATAA TTGGAGAAGA TTTATGTCAG CACACACTTA    3000

CAGAGCACAA ATGCAGTATA TAGGTGCTGG ATGTATGTAA ATATATTCAA ATTATGTATA    3060

AATATATATT ATATATTTAC AAGGAGTTAT TTTTTGTATT GATTTAAAT GGATGTCCCA    3120

ATGCACCTAG AAAATTGGTC TCTCTTTTTT TAATAGCTAT TTGCTAAATG CTGTTCTTAC    3180

ACATAATTTC TTAATTTTCA CCGAGCAGAG GTGGAAAAAT ACTTTTGCTT TCAGGGAAAA    3240

TGGTATAACG TTAATTTATT AATAAATTGG TAATATACAA AACAATTAAT CATTTATAGT    3300

TTTTTTTGTA ATTTAAGTGG CATTTCTATG CAGGCAGCAC AGCAGACTAG TTAATCTATT    3360

GCTTGGACTT AACTAGTTAT CAGATCCTTT GAAAAGAGAA TATTTACAAT ATATGA       3416
```

( 2 ) INFORMATION FOR SEQ ID NO:16:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear -continued ( i i ) MOLECULE TYPE: other nucleic acid ( x i ) SEQUENCE DESCRIPTION: SEQ ID NO:16:

GCTGGTTGTA AG                                                          12

( 2 ) INFORMATION FOR SEQ ID NO:17:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:17:

Ala Gly Cys Lys
1

( 2 ) INFORMATION FOR SEQ ID NO:18:

( i ) SEQUENCE CHARACTERISTICS:
      ( A ) LENGTH: 3 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:18:

Leu Val Val
1

( 2 ) INFORMATION FOR SEQ ID NO:19:

( i ) SEQUENCE CHARACTERISTICS:
      ( A ) LENGTH: 2 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:19:

Trp Leu
1

HUMAN BEK FIBROBLAST GROWTH FACTOR RECEPTOR

This application is a continuation of U.S. Ser. No. 08/323,430, filed Oct. 14, 1994, now pending, which is a continuation of U.S. Ser. No. 07/934,372, filed Aug. 21, 1992, now abandoned, which is a continuation of U.S. Ser. No. 07/549,587, filed Jul. 6, 1990, now abandoned.

FIELD OF THE INVENTION

This invention relates to a unique class of fibroblast growth factor receptors, nucleic acids encoding same and expression of the growth factor receptors in recombinant systems. This invention also relates to the use of the expressed receptors or fragments thereof in screens for candidate drugs which act as receptor antagonists.

REPORTED DEVELOPMENTS

The fibroblast growth factor (FGF) family consists of seven related heparin-binding proteins, which include acidic FGF (aFGF), basic FGF (bFGF). int-2, hst/kFGF, FGF-5, FGF-6 and KGF. The members of the FGF family share approximately 30–55% amino acid sequence identity, similar gene structure, and are capable of transforming cultured cells when overexpressed in transfected cells. The prototypic FGFs, aFGF and bFGF were the first to be purified, sequenced and cloned. They are mitogens, in vitro, for a variety of cells of mesenchymal and neuroectodermal origin. In vivo, FGFs can induce the formation of mesoderm in developing Xenopus embryos and possess potent angiogenic activity (reviewed by Burgess and Maciag, *Ann. Rev. Biochem.* 58: 575–606 (1989)).

The response of cells to FGFs is mediates by binding and activation of specific cell surface receptors possessing intrinsic tyrosine kinase activity. Receptors are proteins, often glycosylated, which serve as integral components of cellular membranes. Typically, receptors possess an extracellular domain located at the cell surface capable of specific interaction with substances known as ligands. The fibroblast growth factors are examples of ligands. As a consequence of the binding of the ligand to the extracellular domain, a second region of the receptor located on the intracellular surface of the membrane (i.e. the cytoplasmic domain), is activated to permit reaction with other intracellular molecules. The cytoplasmic domain comprises a catalytic region, that is a region possessing enzymatic activity. With particular reference to the fibroblast growth factor receptor described herein the catalytic domain is a protein tyrosine kinase. The substrate of this kinase can be the receptor itself (i.e. autophosphorylation) or other intracellular proteins such as phospholipase C-$\gamma$. The kinase domain of certain receptors can be interupted by insertion of up to 100 mostly hydrophilic amino acid residues. This insert may act to modulate receptor interaction with certain cellular substrates and effector proteins. The cytoplasmic domain terminates with a COOH-terminal tail region. This sequence is the most divergent among all known RTRs. Several autophosphorylation sites have been mapped to this region and the region may act by exerting a negative control on kinase signalling function. The catalytic region is separate from membrane proper by a juxtamembrane domain. Present evidence supports the notion that this region is involved in modulation of receptor function by heterologous stimuli, a process known as receptor transmodulation. Linking the extracellular and cytoplasmic domains is a region spanning the membrane proper known as the transmembrane domain. The ligand interaction is thought to activate the cytoplasmic domain by inducing a conformational change such as by aggregation or other mechanisms. Accordingly, a receptor acts as a molecular transducer, translating an extracellular event (ligand binding) into an intracellular response (cytoplasmic enzymatic activity).

As mentioned above, the substance which is bound by the receptor is known as the ligand; a term which is definitionally meaningful only by reference to its counterpart receptor. Accordingly, the term "ligand" does not imply any particular molecule size, structural or compositional feature other than that the substance is capable of binding or otherwise interacting with the receptor in such a manner that the receptor conveys information about the presence of the ligand to an intracellular target molecule. Such a functional definition necessarily excludes substances which may bind to an extracellular domain but fail to affect receptor activation. Stated directly not all substances capable of binding receptors are ligands, but all ligands are capable of binding a receptor.

As mentioned above, receptors have been identified that have assayable biological activity dependent on ligand interaction. Generally, the activity is enzymatic and is localized in the cytoplasmic domain. One group of receptors relevant to this invention possess intrinsic protein tyrosine kinase (PTK) activity.

FIG. 1 presents a schematic representation of several known growth factor receptors that bear PTK activity. Growth factor receptors with PTK activity, or receptor tyrosine kinases (RTKs), have a similar molecular topology. All possess a large glycosylated, extracellular ligand binding domain, a single hydrophobic transmembrane region, and a cytoplasmic domain which contains a PTK catalytic domain. Because of their configuration, RTKs can be envisioned as membrane-associated allosteric enzymes. Unlike water-soluble allosteric enzymes, RTK topology dictates that the ligand binding domain and PTK activity are separated by the plasma membrane. Therefore, receptor activation due to extracellular ligand binding must be translated across the membrane barrier into activation of intracellular domain functions.

On the basis of sequence similarity and distinct structural characteristics, it is possible to classify these receptors into subclasses (FIG. 1). Structural features characteristic of the four subclasses include two cysteine-rich repeat sequences in the extracellular domain of monomeric subclass I receptors, disulfide-linked heterotetrameric $\alpha_2\beta_2$ structures with similar cysteine-rich sequences in subclass II RTKs, and five or three immunoglobulin-like repeats in the extracellular domains of subclass III and IV TRKs, respectively. The tyrosine kinase domain of the latter two subclasses is interrupted by hydrophilic insertion sequences of varying length. The availability of RTK cDNA clones has made it possible to initiate detailed structure/function analyses of the mechanisms of action of RTK family members. (Reviewed by Ullrich & Schlessinger, *Cell* 61: 203–221 (1990))

This invention is predicated on the discovery of a partial human cDNA clone of a fms-like gene (flq) which encoded a protein tyrosine kinase whose kinase domain was interrupted at a position similar to the kinase inserts of the CSF-1 and PDGF receptor tyrosine kinases (Ruta et al., *Oncogene*, 3: 9–15 (1988)). Subsequently, full length cDNAs for chicken flg were isolated by cloning with flg-specific oligonucleotide probes (Lee et al., *Science*, 245: 57–60 (1989)) and with antiphosphotyrosine antibodies (Pasquale and Singer, *Proc. Nat'l. Acad. Sci. USA*, 86: 5449–5453 (1989)).

Flg is an FGF receptor based on four criteria: 1) the receptor purified from a chicken embryo extract by affinity chromatography on immobilized bFGF is the chicken flg gene product, 2) flg anti-peptide antiserum immunoprecipitates [$^{125}$I]aFGF crosslinked to proteins of 130 and 150 kDa in A204 rhabdomyosarcoma cells, 3) flg-anti-peptide antiserum immunoprecipitates proteins of similar size which are specifically phosphorylated on tyrosine upon treatment of living cells with aFGF or bFGF, and 4) proteins of 130 and 150 kDa immunoprecipitated with flg anti-peptide antiserum from aFGF-treated cell lysates undergo tyrosine phosphorylation in vitro.

A putative second FGF receptor is the mouse bacterially expressed kinase (bek) gene product, a partial clone of which was obtained by screening a mouse liver cDNA expression library with anti- phosphotyrosine antibodies (Kornbluth et al., *Mol. Cell. Biol.*, 8: 5541–5544 (1988)). The deduced amino acid sequences of the partial bek clone and the corresponding region of flg are 85% identical. However, it was unclear whether bek represents the mouse homologue of the human flg gene or another closely related gene. This invention provides full length cDNA clones for both human bek and flg, their complete deduced amino acid sequences, and demonstrates in transfected cells that both bek and flg bind aFGF, bFGF and k-FGF specifically and with high affinity.

Receptor function has increasingly become the focus of attempts to rationally design drugs. Molecules that affect receptor-ligand binding, receptor activation and/or receptor intracellular target interaction are all potential candidates for therapeutics. Large scale screening is limited by conventional methods in which candidate drugs are tested on isolated cells or tissue explants. Tissue samples or isolated cells containing the target receptors are costly to obtain, present in limited quantxty and difficult to maintain in a functionally viable state. Additionally, it is often difficult to reliably and reproducibly administer the candidate drug to tissue samples. Screening assays using primary explants in tissue culture are undertaken in larger scale than is possible with tissue samples. However, it is more difficult to assay physiological effect and the assays are subject to interference from many sources, e.g. culture media or cultivation conditions. Finally, assays using receptors isolated from natural materials have the disadvantage that the receptor is subject to natural variability and suitable natural sources may not always be available. It is an object herein to provide receptor molecules in a form amendable for large scale screening protocols.

SUMMARY OF THE INVENTION

This invention provides a receptor protein or fragments thereof, in isolated form, comprising a cytoplasmic domain with protein kinase activity, a kinase insert, a transmembrane domain and an extracellular domain having three immunoglobulin-like repeats and biologically active equivalents thereof.

Another aspect of this invention is an isolated DNA sequence encoding a receptor protein or fragments thereof, said protein having a cytoplasmic domain with protein kinase activity, a kinase insert, a single transmembrane domain and an extracellular domain having three immunoglobulin-like repeats and biologically equivalents thereof.

Another aspect of this invention is a vector comprising a cDNA encoding a receptor protein, said protein having a cytoplasmic domain with protein kinase activity, a kinase insert, a single transmembrane domain and an extracellular domain having three immunoglobulin-like repeats.

Another aspect of this invention is a host cell transformed with the above-described vector.

Another aspect of this invention is a therapeutic composition comprising the extracellular domain or fragment thereof of a human receptor protein comprising a cytoplasmic domain having protein kinase activity, a kinase insert, a single transmembrane domain and an extracellular domain having three immunoglobulin-like repeats in an amount effective to inhibit undesirable heparin-binding growth factor mediated cellular responses and a pharmaceutical acceptable carrier.

Another aspect of this invention is a therapeutuc composition comprising the extracellular domain or fragment thereof of a human receptor protein comprising a cytoplasmic domain having protein kinase activity, a kinase insert, a single transmembrane domain and an extracel-lular domain having three immunoglobulin-like repeats in an amount effective to inhibit the binding of an opportunistic pathogen to human cells bearing said receptor protein and a pharmaceutical acceptable carrier.

Another aspect of this invention is a method for the treatment of a patient with a disease characterized by an undesirable heparin-binding growth factor mediated cellular response comprising administering to such patient an effective amount of the the composition of claim 25.

Another aspect of this invention is a method for the treatment of a patient suffering from an opportunistic pathogen infection said pathogen being capable of binding to a heparin-binding growth factor receptor comprising administering to such patient an effective amount of the composition of claim 29.

Another aspect of the invention is a method for the screening of drugs that inhibit fibroblast growth factor binding to cellular receptors comprising the steps of:
 (a) incubating the drug with host cells capable of overexpressing fibroblast growth factor receptors in the presence of a fibroblast growth factor and
 (b) measuring the ability of the drug to inhibit fibroblast growth factor binding.

A final aspect of the invention is a method for screening of drugs that inhibit the binding of opportunistic pathogens to fibroblast growth factor receptors comprising the steps of:
 (a) incubating the drug with host cells capable of overexpressing fibroblast growth factor receptors in the presence of said pathogen and
 (b) measuring the ability of the drug to inhibit pathogen binding.

Figure 1:
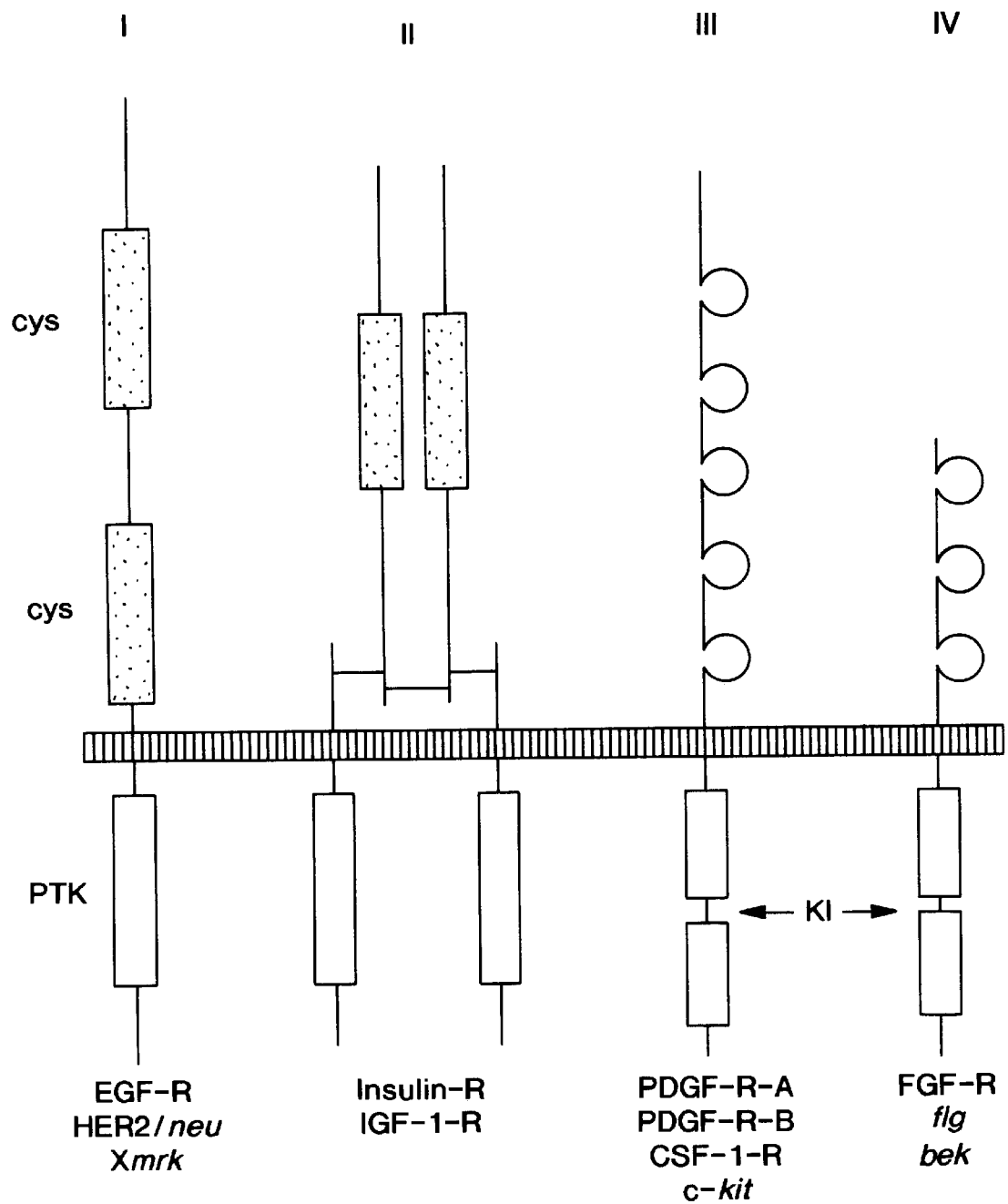
FIG. 1 presents a schematic representation of receptor tyrosine kinase subclasses.

A) The amino acid sequences of human flg and bek as deduced from the CDNA clones is presented. Only residues in the bek sequence which differ from those in flg are shown. The solid overlines highlight the postulated signal peptide and transmembrane sequences while the dashed overline highlights the kinase insert region. A solid dot is placed over conserved cysteine residues which define Ig-like domains. Inverted triangles are placed over potential Asn-linked glycosylation sites. The open brackets surround the "acidic box" and the opposing arrows demarcate the tyrosine kinase domain.

B) The degree of amino acid identity between different regions of the human bek and flg proteins is illustrated. The solid block boxes represent the split cytoplasmic kinase domain and the loops represent the extracellular Ig-like domains. The nucleotide sequences have been submitted to the EMBL Data Library. Accession numbers X52832 and X52833 have been assigned to human bek and flg cDNAs respectively.

FIG. 3 illustrates a Northern Blot evidencing flg and bek mRNA expression.

Four μg of total RNA from various cell lines was subjected to Northern analysis for flg expression (Panel A) or bek expression (Panel B). An illustration of an autoradiogram of the resulting blots is shown. The RNAs are from the cell lines: A204 rhabdomyosarcoma (lane 1); U563 glioblastoma (lane 2); HUVEC (lane 3); NTERA-2 teratocarcinoma (lane 4).

FIG. 4 illustrates the metabolic labeling of flg and bek overexpressing cell lines with [$^{35}$S] methionine.

NFlg26, NBek8 and NNeo4 control cells were labeled with [$^{35}$S] methionine in the presence (lanes 2, 4, 6, 8) or absence (lanes 1, 3, 5, 7) of tunicamycin as described in Example II. The cell lysates were immunoprecipitated with anti-flg-1 (lanes 1–4) or anti-bek-1 (lanes 5–8) and subjected to SDS-PAGE and autoradiography. An illustration of the resulting autoradiogram is shown. The lysates are from: Neo 4 control cells (lanes 1, 2, 5, 6); Flg 26 cells (lanes 3, 4); Bek 8 cells (lanes 7, 8). The positions of molecular weight standards are indicated. Immunoprecipitation in the presence of the corresponding antigenic peptide completely eliminates the precipitation of the flg and bek specific proteins (data not shown).

FIG. 5 illustrates the crosslinking of [$^{125}$I]FGFs to flg and bek overexpressing cells.

A) [$^{125}$I]aFGF (lanes 1–3) and [$^{125}$I]bFGF (lanes 4–6) were covalently crosslinked to monolayers of NFlg26 (lanes 3,6), NBek8 (lanes 3,6) and NNeo4 control (lanes 1,4) cells as described in Example III. The cells were then lysed, subjected to SDS-PAGE and the gel was exposed to X-ray film. An illustration of the resulting autoradiogram is shown.

Figure 5A:
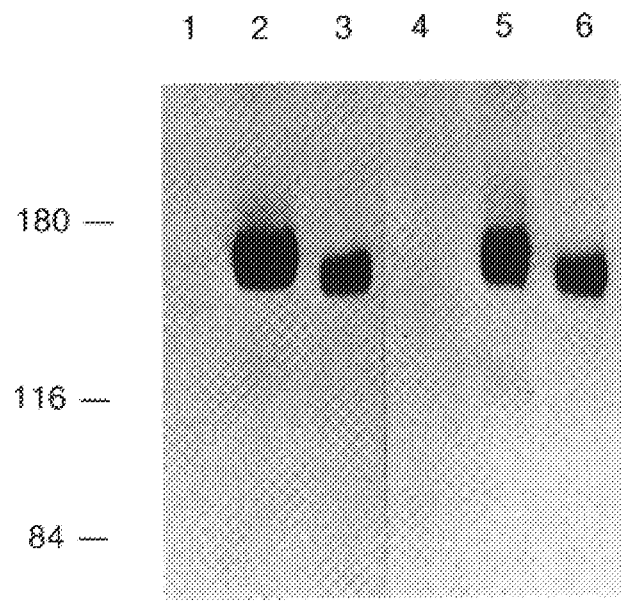

B) [$^{125}$I]aFGF (lanes 1–3) and [$^{125}$I]kFGF (lanes 4–6) were covalently crosslinked to monolayers of NNeo4 (lanes 1,4), NFlg26 (lanes 2,5) and NBek13 (lanes 3,6) and analyzed as in FIG. 5A.

FIG. 6 illustrates a scatchard analysis of FGF binding to flg and bek overexpressing cell lines.

A) Saturation binding analysis of [$^{125}$I]aFGF (■——■) and [$^{125}$I]bFGF (●——●) to flg26 (Panel A) and bek8 (Panel B) cells was performed as outlined in Example III. The background counts in the presence of a 100 fold molar excess of either ligand was always less than 10% of the total cpm at each point. The scale on the Scatchard analysis is the same in each panel.

B) Saturation binding analysis of [$^{125}$I]kFGF to flg26 (panel A) and to bek13 (panel B). Analysis as in FIG. 6A.

FIG. 7 illustrates the complete nucleotide [SEQ ID NO: 14] and amino acid [SEQ ID NO: 12] sequence of flg.

FIG. 8 illustrates the complete nucleotide [SEQ ID NO: 15] and amino acid [SEQ ID NO: 13] sequence of bek.

DETAILED DESCRIPTION OF THE INVENTION

As used herein the following terms have the following meanings:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and the combination of base and sugar is called a nucleoside. The base characterizes the nucleoside. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses. Heterologous DNA is DNA which can be introduced into a host organism from a source that does not normally exchange DNA with that host. e.g. human DNA used to transform E. coli.

Codon—A DNA sequence of three nucleotides (a triplet) which encodes through mRNA an amino acid, a translation start signal or a translation termination signal. For example, the DNA nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the DNA sequence GCTGGTTGTAAG(SEQ ID NO: 16) theoretically may be expressed in three reading frames or phases, each of which affords a different amino acid sequence:

GCT GGT TGT AAG--Ala-Gly-Cys-Lys (SEQ ID NOS: 16 and 17)

G CTG GTT GTAAG-Leu-Val-Val (SEQ ID NOS: 16 and 18)

GC TGG TTG TAA G--Trp-Leu (SEQ ID NOS: 16 and 19)-(STOP)

However, only one of the above reading frames encodes the correct genetic information. The translational start signal is recognized by the ribosome and accessory initiation factors to fix the correct reading frame.

Polypeptide—A linear array of amino acids connected one to the other by peptide bonds between the α-amino and carboxy groups of adjacent amino acids.

Genome—The entire DNA of a cell or a virus. It includes inter alia the structural genes coding for individual polypeptides as well as regulatory sequences such as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide. Structural genes may also have RNAs as their primary product such as transfer RNAs (tRNAs) or ribosomal RNAs (rRNAs).

Transcription—The process of producing RNA from a structural gene.

Translation—The process of producing a polypeptide from mRNA.

Expression—The process undergone by a structural gene to produce a product. In the case of a protein product it is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant".

Phage or Bacteriophage—Bacterial virus many of which consist of DNA sequences encapsulated in a protein envelope or coat ("capsid").

Cloning Vehicle—A plasmid, phage DNA or other DNA sequence which is able to replicate in a host cell, characterized by one or a small number of endonuclease recognition sites at which such DNA sequences may be cut in a determinable fashion for the insertion of heterologous DNA without attendant loss of an essential biological function of the DNA, e.g., replication, production of coat proteins or loss of expression control regions such as promoters or binding sites, and which contain a selectable gene marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction or DNA replication.

Replicon—DNA required for replication in a particular organism, includes an origin of replication.

Recombinant DNA Molecule—A molecule consisting of segments of DNA from different genomes which have been joined end-to-end and have the capacity to infect some host cell and be maintained therein.

Expression Control Sequence—A sequence of nucleotides that controls and regulates expressing of structural genes when operatively linked to those genes. They include the lac system, major operator and promoter regions of phage lambda, the control region of viral coat proteins and other sequences known to control the expression of genes of prokaryotic or eukaryotic cells and their viruses.

Mutation—A hereditable change in the genetic information of an organism.

Mutant—An organism harboring a mutation. Generally expressing a discernible phenotype when compared to a standard reference strain of the species to which the organism belongs or to a wild-type population of that organism.

As used herein, bek and flg denotes fibroblast growth factor receptors or their fragments produced by cell or cell-free culture systems, in bioactive forms having the capacity to influence cellular growth, differentiation and response in vitro as does native bek and flg.

Different alleles of bek and flg may exist in nature. These variations may be characterized by differences in the nucleotide sequence of the structural gene coding for proteins of identical biological function. It is possible to produce analogs having single or multiple amino acid substitutions, deletions, additions or replacements. All such allelic variations, modifications and analogs including alternative mRNA splicing forms resulting in derivatives of bek and flg which retain any of the biologically active properties of native bek and flg are included within the scope of this invention.

The one and three-letter amino acid abbreviations used herein have the following meanings:

| A | Ala | Alanine |
|---|-----|---------|
| C | Cys | Cysteine |
| D | Asp | Aspartic Acid |
| E | Glu | Glutamic Acid |
| F | Phe | Phenylalanine |
| G | Gly | Glycine |
| H | His | Histidine |

-continued

| I | Ile | Isoleucine |
|---|-----|------------|
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| B | Asx | Asp or Asn, not distinguished |
| Z | Glx | Glu or Gln, not distinguished |
| X | X | Undetermined or atypical amino acid |

For ease of explanation this invention may be envisioned as having three separate but interrelated embodiments. A first embodiment involves the cloning and identification of full length cDNAs encoding human flg and bek receptor protein. A second embodiment constitutes the expression of human flg and bek gene products in recombinant host cells and a third embodiment constitutes the use of the recombinantly derived products for, inter alia, receptor analysis and drug screening.

Cloning of human flg and bek

In general, recombinant DNA techniques are known. (See: *Methods In Enzymology*, (Academic Press, New York Volumes 65 and 68 (1979); 100 and 101 (1983)) and the references cited therein. An extensive technical discussion embodying most commonly used recombinant DNA methodologies can be found in Maniatis, et al., *Molecular Cloning*, Cold Spring Harbor Laboratory (1982) and in *Current Protocols in Molecular Biology*, Vols. I and II, Ausubel, et al. eds., Greene Publishing Assoc. and Wiley Interscience, (1987). Genes coding for various polypeptides may be cloned by incorporating a DNA fragment coding for the polypeptide in a recombinant DNA vehicle, e.g., bacterial or viral vectors, and transforming a suitable host. This host is typically an *Escherichia coli* (*E. coli*) strain, however, depending upon the desired product, eukaryotic hosts may be utilized. Clones incorporating the recombinant vectors are isolated and may be grown and used to produce the desired polypeptide on a large scale.

Several groups of workers have isolated mixtures of messenger RNA (mRNA) from eukaryotic cells and employed a series of enzymatic reactions to synthesize double-stranded DNA copies which are complementary to this mRNA mixture. (Wewer, et al., *Proc. Nat'l. Acad. Sci. USA*, 83: 7137–7141 (1986)). In the first reaction, mRNA is transcribed into a single-stranded complementary DNA (cDNA) by an RNA-directed DNA polymerase, also called reverse transcriptase. Reverse transcriptase synthesizes DNA in the 5'–3' direction, utilizes deoxyribonucleoside 5'-triphosphates as precursors, and requires both a template and a primer strand, the latter of which must have a free 3-hydroxyl terminus. Reverse transcriptase products, whether partial or complete copies of the mRNA template, often possess short, partially double-stranded hairpins ("loops") at their 3' termini. In the second reaction, these "hairpin loops" can be exploited as primers for DNA polymerases. Preformed DNA is required both as a template and as a primer in the action of DNA polymerase. The DNA polymerase requires the presence of a DNA strand having a free 3'-hydroxyl group, to which new nucleotides are added to extend the chain in the 5'–3' direction. The products of such sequential reverse transcriptase and DNA polymerase reactions still possess a loop at one end. The apex of the loop or "fold-point" of the double-stranded DNA, which has thus been created, is substantially a single-strand segment. In the third reaction, this single-strand segment is cleaved with the single-strand specific nuclease Si to generate a "blunt-end" duplex DNA segment. This general method is applicable to any mRNA mixture, and is described by Buell, et al., *J. Biol. Chem.*, 253: 2483 (1978).

The resulting double-stranded cDNA mixture (ds-cDNA) is inserted into cloning vehicles by any one of many known techniques, depending at least in part on the particular vehicle used. Various insertion methods are discussed in considerable detail in *Methods In Enzymology*, 68: 16–18 (1980), and the references cited therein.

Once the DNA segments are inserted, the cloning vehicle is used to transform a suitable host. These cloning vehicles usually impart an antibiotic resistance trait on the host. Such hosts are generally prokaryotic cells. At this point, only a few of the transformed or transfected hosts contain the desired cDNA. The sum of all transformed or transfected hosts constitutes a gene "library". The overall ds-cDNA library created by this method provides a representative sample of the coding information present in the mRNA mixture used as the starting material.

If an appropriate oligonucleotide sequence is available, it can be used to identify clones of interest in the following manner. Individual transformed or transfected cells are grown as colonies on a nitrocellulose filter paper. These colonies are lysed; the DNA released is bound tightly to the filter paper by heating. The filter paper is then incubated with a labeled oligonucleotide probe which is complementary to the structural gene of interest. The probe hybridizes with the cDNA for which it is complementary, and is identified by autoradiography. The corresponding clones are characterized in order to identify one or a combination of clones which contain all of the structural information for the desired protein. The nucleic acid sequence coding for the protein of interest is isolated and reinserted into an expression vector. The expression vector brings the cloned gene under the regulatory control of specific prokaryotic or eukaryotic control elements which allow the efficient expression (transcription and translation) of the ds-cDNA. Thus, this general technique is only applicable to those proteins for which at least a portion of their amino acid or DNA sequence is known for which an oligonucleotide probe is available. See, generally, Maniatis, et al., supra.

More recently, methods have been developed to identify specific clones by probing bacterial colonies or phage plaques with antibodies specific for the encoded protein of interest. This method can only be used with "expression vector" cloning vehicles since elaboration of the protein product is required. The structural gene is inserted into the vector adjacent to regulatory gene sequences that control expression of the protein. The cells are lysed, either by chemical methods or by a function supplied by the host cell or vector, and the protein is detected by a specific antibody and a detection system such as enzyme immunoassay. An example of this is the $\lambda gt_{11}$ system described by Young and Davis, *Proc. Nat'l. Acad. Sci. USA*, 80: 1194–1198 (1983) and Young and Davis, *Science*, 222: 778 (1983).

As mentioned above, a partial cDNA clone of human flg was known from the present inventors' previous work. Subsequent nucleotide sequence analysis of the original human flg partial cDNA clone C51, as well as several additional independent isolates revealed that all of the partial clones had the identical 5' sequence, corresponding to a cleaved, naturally occurring EcoRI site. This suggested that, in the construction of the CDNA library, this EcoRI site was not protected by EcoRI methylase prior to cleavage with EcoRI. It was reasoned, therefore, that the 5' end of flg cDNA resided on an independently cloned, non-overlapping EcoRI fragment. The anchored Polymerase Chain Reaction (PCR) technique (Loh, et al., *Science*, 243: 217–220 (1989)) was used to confirm this and to obtain an additional 170 base pairs (bp) of flg nucleotide sequence upstream of the internal EcoRI site. A second round of PCR reactions using primers in this new sequence together with $\lambda gt_{11}$ arm-specific oligonucleotide primers amplified the insert of a 5' flg clone from the same HUVEC cDNA library. Because PCR-generated sequence mutations have occasionally been encountered, this second PCR product was radiolabelled and used as a probe to rescreen the HUVEC cDNA library in $\lambda gt_{11}$. One 700 bp clone was obtained which extended from the internal EcoRI site into the 5' untranslated region. The complete deduced amino acid sequence of human flg is shown in FIG. 2A.

The published sequences of the partial mouse bek and human flg cDNA clones (Kornbluth, et al., 1988 supra; Ruta, et al., 1988 supra) are highly homologous with significant divergence found only in the kinase insert (50% identity) and at the COOH terminus. Although the small sequence differences could have been attributed to species divergence, it was noted that the much larger kinase inserts of the human and murine PDGF receptors (B type) are 85% identical (Yarden, et al., *Nature*, 323: 226–232 (1986); Claesson-Welsh, et al., *Mol. Cell. Biol.*, 8: 3476–3486 (1988)) suggesting that bek might actually be a different gene product than flg. To clone bek, a human brainstem cDNA library in $\lambda gt_{11}$ was screened with a radiolabelled 33 base oligonucleotide corresponding to the COOH-terminal 11 codons of mouse bek (Kornbluth, et al., 1988 supra). This corresponds to the longest stretch of non-identity between the published bek and flg sequences. Thirty-two clones were identified, of which one, bek5, containing a 3.2 kb cDNA insert was sequenced. The deduced amino acid sequence clearly established that it was very similar to, but distinct from flg, and that is lacked approximately 25 bp of signal peptide sequence, including the translation initiating ATG. Overlapping clones were obtained by rescreening the brainstem library with a 750 bp cDNA fragment corresponding to the 5' region of bek 5. The complete deduced amino acid sequence of human bek is shown in FIG. 2A. The specific details of flg and bek cloning appear in Example I.

Flg and bek are similar yet distinct gene products (FIG. 2B), with structural features shared by the PDGF/CSF-1/c-kit family of receptor linked tyrosine kinases (Ullrich and Schlessinger, 1990 supra). Their coding sequences consist of a hydrophobic signal peptide sequence of 21 amino acids, an extracellular domain of 356 (bek) and 355 (flg) amino acids, a transmembrane domain of 21 amino acids and an cytoplasmic domain of 423 (bek) and 425 (flg) amino acids. The extracellular domains of flg and bek contain 3 "immunoglobulin-like" (Ig) domains of similar size and location. Interestingly, the amino acid sequence identity within and surrounding the first Ig domains is much less (43%) than that found within and surrounding the second and third Ig domains (74%). Eight potential N-linked glycosylation sites are located at identical positions in the extracellular domains of flg and bek. Flg contains an additional N-linked glycosylation site at amino acid 185. Lee, et al. (1989) have noted a region in the extracellular domain of chicken flg with 8 neighboring acidic amino acids. This "acidic box" is also present in human flg and human bek, and consists of 8 and 5 acidic residues, respectively. The cytoplasmic domains of bek and flg consist of long juxtamembrane regions followed by conserved catalytic kinase domains which are split by 14 amino acid insertions. The kinase domains are followed by divergent carboxy terminal tails. The overall identity between bek and flg is 71%, with the region of highest identity (88%) being the kinase domain.

Figure 2B:
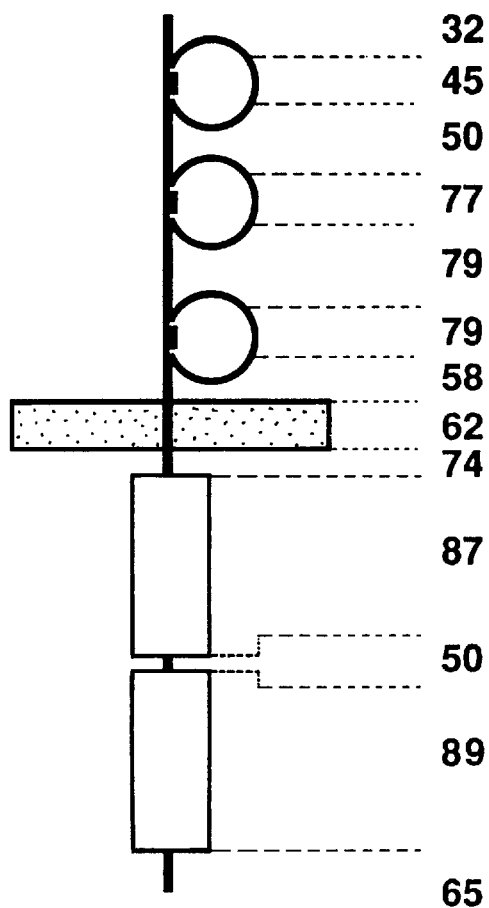
FIG. 2 illustrates the amino acid sequences and structural similarities of human flg [SEQ ID NO: 12] and bek [SEQ ID NO: 13].

Flg and bek mRNA expression in various cell lines was determined by Northern blot analysis with bek and flg cDNA probes corresponding to a portion of their non-homologous 3' untranslated regions. In A204 rhabdomyosarcoma cells, two flg transcripts of approximately 4.3 and 4.2 kb are observed, but bek mRNA is undetectable (FIG. 3). HUVEC and human teratocarcinoma NTERA2 cells uniquely express the 4.2 and 4.3 kb flg transcripts, respectively. The significance of the distinct 4.3 and 4.2 kb flg transcripts is presently unknown. They may be related to flg clones which have been isolated that when compared to FIG. 2A and 2B, are deleted of the amino-terminal cysteine loop of the extracellular domain. A 4.4 kb bek transcript was observed only in the teratocarcinoma cell line. Other workers have shown that bek mRNA is expressed in adult mouse liver, lung, brain and kidney but is absent from heart and spleen (Kornbluth, et al., 1988 supra). The chicken flg protein was found in embryonic intestine, brain, gizzard, heart, skeletal muscle and fibroblasts, but only in the brain of adult chickens (Pasquale and Singer, *Proc. Nat'l. Acad. Sci. USA*, 86: 5449–5453 (1989)). Taken together, these results demonstrate that bek and flg are not expressed coordinately.

Expression of flg and bek in recombinant cells

The flg and bek ds-cDNAs can be inserted into expression vectors by any one of many known techniques. In general, methods can be found in Maniatis, et al. (1982), supra, and Ausubel, et al. (1987), supra. In general, the vector is linearized by at least one restriction endonuclease, which will produce at least two blunt or cohesive ends. The ds-cDNA is ligated with or joined into the vector insertion site.

If prokaryotic cells or other cells which contain substantial cell wall material are employed, the most common method of transformation with the expression vector is calcium chloride pretreatment as described by Cohen, R. N., et al., *Proc. Nat'l. Acad. Sci. USA*, 69: 2110 (1972). If cells without cell wall barriers are used as host cells, transfection is carried out by the calcium phosphate precipitation method described by Graham and Van der Eb, *Virology*, 52: 456 (1973). Other methods for introducing DNA into cells such as nuclear injection, viral infection, electroporation or protoplast fusion may be successfully used. The cells are then cultured on selective media, and proteins for which the expression vector encodes are produced.

"Expression vectors" refer to vectors which are capable of transcribing and translating DNA sequences contained therein, where such sequences are linked to other regulatory sequences capable of affecting their expression. These expression vectors must be replicable in the host organisms or systems either as episomes, bacteriophage, or as an integral part of the chromosomal DNA. One form of expression vector is the bacteriophage, viruses which normally inhabit and replicate in bacteria. Particularly desirable phage for this purpose are the $\lambda gt_{10}$ and $\lambda gt_{11}$ phage described by Yound and Davis, supra. $\lambda gt_{11}$ is a general recombinant DNA expression vector capable of producing polypeptides specified by the inserted DNA.

To minimize degradation, upon induction with a synthetic analogue of lactose (IPTG), foreign proteins or portions thereof are synthesized fused to the prokaryotic protein β-galactosidase. The use of host cells defective in protein degradation pathways may also increase the lifetime of novel proteins produced from the induced $\lambda gt_{11}$ clones. Proper expression of foreign DNA in $\lambda gt_{11}$ clones will depend upon the proper orientation and reading frame of the inserted DNA with respect to the β-galactosidase promoter and translation initiating codon.

Another form of expression vector useful in recombinant DNA techniques is the plasmid—a circular unintegrated (extra-chromosomal), double-stranded DNA. Any other form of expression vector which serves an equivalent function is suitable for use in the process of this invention. Recombinant vectors and methodology disclosed herein are suitable for use in host cells covering a wide range of prokaryotic and eukaryotic organisms. Prokaryotic cells are preferred for the cloning of DNA sequences and in the construction of vectors. For example, *E. coli* K12 strain HB101 (ATCC No. 339694), is particularly useful. Of course, other microbial strains may be used. Vectors containing replication and control sequences which are derived from species compatible with the host cell or system are used in connection with these hosts. The vector ordinarily carries an origin of replication, as well as characteristics capable of providing phenotypic selection in transformed cells. For example, *E. coli* can be transformed using the vector pBR322, which contains genes for ampicillin and tetracycline resistance (Bolivar, et al., *Gene*, 2:95 (1977)).

These antibiotic resistance genes provide a means of identifying transformed cells. The expression vector may also contain control elements which can be used for the expression of the gene of interest. Common prokaryotic control elements used for expression of foreign DNA sequences in *E. coli* include the promoters and regulatory sequences derived from the β-galactosidase and tryptophan (trp) operons of *E. coli*, as well as the pR and pL promoters of bacteriophage λ. Combinations of these elements have also been used (e.g., TAC, which is a fusion of the trp promoter with the lactose operator). Other promoters have also been discovered and utilized, and details concerning their nucleotide sequences have been published enabling a skilled worker to combine and exploit them functionally.

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. Yeast promoters suitable for the expression of foreign DNA sequences in yeast include the promoters for 3-phosphoglycerate kinase or other glycolytic enzymes. Suitable expression vectors may contain termination signals which provide for the polyadenylation and termination of the mRNA transcript of the cloned gene. Any vector containing a yeast-compatible promoter, origin of replication and appropriate termination sequence is suitable for expression of bek or flg.

Cell lines derived from multicellular organisms may also be used as hosts. In principle, any such cell culture is workable, whether from a vertebrate or invertebrate source. However, interest has been greatest in vertebrate cells, and propagation of vertebrate cells in culture (tissue culture) has become a routine procedure in recent years. Examples of such useful hosts are the VERO, HeLa, mouse C127 or 3T3, Chinese hamster ovary (CHO), WI38, BHK, COS-7, and MDCK cell lines. Mouse 3T3 and CHO cells are particularly preferred. Expression vectors for such cells ordinarily include an origin or replication, a promoter located in front of the gene to be expressed, RNA splice sites (if necessary), and transcriptional termination sequences.

For use in mammalian cells, the control functions (promoters and enhancers) on the expression vectors are often provided by viral material. For example, commonly used promoters are derived from polyoma, Adenovirus 2, and most frequently, Simian Virus 40 (SV40). Eukaryotic promoters, such as the promoter of the murine metallothionein gene (Paulakis and Hamer, *Proc. Nat'l. Acad. Sci.*, 80: 397–401 (1983)), may also be used. Further, it is also possible, and often desirable, to utilize the promoter or control sequences which are naturally associated with the desired gene sequence, provided such control sequences are compatible with the host system. To increase the rate of transcription, eukaryotic enhancer sequences can also be added to the construction. These sequences can be obtained from a variety of animal cells or oncogenic retroviruses such as the mouse sarcoma virus.

An origin of replication may be provided either by construction of the vector to include an exogenous origin, such as that provided by SV40 or other viral sources, or may be provided by the host cell chromosomal replication mechanism. If the vector is integrated into the host cell chromosome, the latter is often sufficient.

Host cells can yield bek or flg which can be of a variety of chemical compositions. The protein is produced having methionine as its first amino acid. This methionine is present by virtue of the ATG start codon naturally existing at the origin of the structural gene or by being engineered before a segment of the structural gene. The protein may also be intracellularly or extracellularly cleaved, giving rise to the amino acid which is found naturally at the amino terminus of the protein. The protein may be produced together with either its own or a heterologous signal peptide, the signal polypeptide being specifically cleavable in an intra- or extracellular environment. Finally, bek or flg may be produced by direct expression in mature form without the necessity of cleaving away any extraneous polypeptide.

Recombinant host cells refer to cells which have been transformed with vectors constructed using recombinant DNA techniques. As defined herein, bek or flg is produced as a consequence of this transformation. bek or flg or their fragments produced by such cells are referred to as "recombinant bek or flg".

The details of the expression of flg and bek are given in Example II.

Applications of flg and bek over producing cell lines

The over-expressing bek and flg cell lines provided herein are useful for investigation of ligand/reception interaction as well as in a screening program for rationally designed drugs. Potential sites of action for therapeutics include but are not limited to receptor/ligand binding, signal transduction, receptor/target interaction.

Accordingly, drugs may be tested for their ability to inhibit natural ligand binding by competitive inhibition or other mechanisms. Alternatively, the bek and flg overproducing cells may be used as an immunogen source to produce antibodies, such as monoclonal antibodies, which also may be tested for their ability to affect ligand binding or receptor aggregation. The system may also be used to evaluate drugs that affect the kinase/target interactions. These drugs, known as tyrphostins have as their site of action the phosphorylation of cellular targets by the receptor kinase domain, including the autophosphorylation of the receptor itself. Because the ligand binding and kinase activity reside in separate domains, it is not necessary to express the entire receptor sequence in order to evaluate the effects of drugs on the above-identified activities. Accordingly, this invention contemplates the expression of biologically active fragments of flg and bek. For example, the products of the cloning and expression of cDNA encoding the first 377 amino acids of bek or first 376 amino acids of flg (i.e. the extracellular plus transmembrane domains) or COOH terminal 423 amino acids of bek or 425 amino acids of flg may be usefully employed the evaluate ligand and tryphostins respectively. Example III illustrates several of these applications.

In yet another embodiment, the extracellular domain alone or sub-domains thereof may be useful as inhibitors of infection by opportunistic pathogens such as Herpes Simplex Virus type I or other pathogens which use endogenous bek or flg as a means of infecting its target cell. It has been reported that HSV-1 entry into cells is dramatically increased in cell lines which have overexpressed flg on their surface (R. J. Kaner, et al., *Science* 248: 1410–1413 (1990)). Accordingly, the over-expressing cell lines may be used to screen inhibitor drugs by measuring reduced virus binding (direct assay) or by reduced infectivity or reduction of virus from media in the presence or absence of candidate drugs such as receptor fragments themselves.

This invention provides the complete human cDNA sequences for two fibroblast growth factor receptors. Although a partial cDNA sequence of a human protein kinase terminal flg was known (Ruta, et al., supra, (1988)) as was the partial sequence of the mouse protein kinase bek (Kornbluth, et al., supra, (1988)), the complete sequences of the human forms of these genes were not available. Without the complete sequences the extent of the functional ligand binding site and the degree of homology between flg and bek could not be properly evaluated. As disclosed herein, flg and bek are similar but distinct gene products which have high affinity for aFGF, bFGF and k-FGF. The bek and flg genes are located on different chromosomes and are differentially expressed in various cell lines and tissues.

Flg and bek exhibit structural features shared by the PDGF and CSF-1 receptor tyrosine kinases including a split tyrosine kinase domain and an extracellular region consisting of multiple immunoglobulin-like domains. However, the FGF receptors are structurally distinct from the PDGF and CSF-1 receptors in several respects: 1) the extracellular domains of the FGF receptors consist of 3 immunoglobulin (Ig) domains, whereas those of the PDGF and CSF-1 receptors consist of 5 Ig domains. In this regard the FGF receptors resemble the IL-1 receptor, whose extracellular region consists of-three Ig domains (Sims, et al., *Science*, 241: 585–589 (1988)); 2) the juxtamembrane region of the FGF receptors, 87 (flg) and 89 (bek) amino acids, is significantly longer than that of the PDGF and CSF-1 receptors (49- and 51- amino acids respectively); 3) the kinase insert domain of the FGF receptors consists of only 14 amino acids whereas the PDGF and CSF-1 receptor kinase inserts are much larger (104- and 70- amino acids respectively) (Hanks, et al., *Science*, 241: 42–52 (1988)). A consensus tyrosine residue and potential autophosphorylation site in the kinase domain of the PDGF receptor is conserved in both FGF receptors (flg residue 654, bek residue 657). The presence of common motifs among the receptors for a variety of biologically distinct ligands supports the argument that, for reasons of structure and/or function, then have been subject to strong evolutionary constraints (Ullrich and Schlessinger, *Cell* 60: 203–221 (1990)).

NIH 3T3 cells transfected with mammalian expression vectors containing the coding sequences of either flg or bek direct the synthesis of glycoproteins with apparent molecular weights of 150,000 and 135,000 respectively. When synthesized in the presence of tunicamycin, the molecular weight of the major flg protein is 110 kDa while that of bek is 90 kDa. Two flg proteins of 90 and 110 kDa had been previously observed in immunoprecipitates of tunicamycin-treated, metabolically labeled human rhabdomyosarcoma cells (Ruta, et al., *Proc. Nat'l. Acad. Sci. USA*, 86: 8722–8726 (1989)). Although it is impossible to completely rule out a mechanism involving proteolysis, the 90 and 110 kDa flg proteins in rhabdomyosarcoma cells may represent genuine primary translation products. Reid, et al. (*Proc. Nat'l. Acad. Sci. USA*, 87: 1596–1600 (1990)) recently reported the isolation of two distinct murine flg cDNAs, one of which is apparently the homolog of the human flg cDNA disclosed herein, and a second shorter cDNA which is deleted of the region encoding the first Ig-like domain by alternative splicing. In addition to the full length clones disclosed herein, other cDNA clones can be recovered which appear to encode truncated forms of flg and bek from HUVEC and human brain cDNA libraries. A variant of flg lacking the first Ig-like domain, but otherwise intact was isolated. Other cDNA variants include a truncated version of bek encoding only a single sequence, a single "Ig-like" domain and a stop codon and a variant of flg encoding two "Ig-like" domains. These two clones may represent secreted forms of bek or flg. Comparison of the nucleotide sequences of these clones to flg and bek cDNAs encoding receptors with three "Ig-like" domains suggests that they were derived from the structural genes of flg and bek by alternatiave splicing. It is possible, therefore, that the lower molecular weight species of flg immunoprecipitated from lysates of rhabdomyosarcoma cells represents a genuine form of flg which was generated by alternative splicing. Interestingly, the A204 rhabdomyosarcoma cells express two different flg mRNAs which might represent the alternatively spliced forms, whereas the NTERA-2 and endothelial cells appear to differentially express the alternative flg mRNAs.

Deposit of Strains Useful in Practicing the Invention

A deposit of biologically pure culture of the following strain was made with the American Type Culture Collection, 12301 Parklawn Drive, Rockville, Md., the accession number indicated was assigned after successful viability testing, and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Strain/Plasmid | ATCC No. | Deposit Date |
|---|---|---|
| *E. coli*/pGC37 | 68370 | July 20, 1990 |
| *E. coli*/pflgFL24 | 68369 | July 20, 1990 |

It should be noted that for ease of storage the vectors of the present invention have been deposited in the form of transformed bacterial hosts. It is a matter of routine skill however for a recipient to culture the bacterial cells, recovering the vectors and use same to transform other host cells such as mouse 3T3 cells as described herein.

The following examples are given as illustrative of the present invention. The present invention is not restricted only to these examples.

EXAMPLE I

This example illustrates the cloning of full length flg and bek cDNAs. As mentioned above, a partial clone was isolated by screening a cDNA library derived from human endothelial mRNA with a probe based on a retroviral transforming gene product. (See Ruta, et al., 1988 supra for details). Specifically the V-fms oncogene (the activated form of the CSF-1 tyrosine kinase receptor) was employed as a probe to screen $10^6$ plaques under low stringency. Fifteen positive $\lambda gt_{11}$ clones were detected, and five were plaque purified and analyzed further. One clone, C51, was denominated fms-like gene (flg). As described herein below, the missing 5' fragment was recovered by a combination of PCR and conventional cloning techniques.

PCR Amplification and oligonucleotide Primers

The Polymerase Chain Reaction (PCR) technique (Saiki, et al., *Science*, 230: 1350–1354 (1985)) was performed with 100 pmol each oligonucleotide primer, 50 mM KCl, 1.5 mM $MgCl_2$, 0.01% gelatin, 0.2 mM each of dATP, dGTP, dCTP and dTTP, 10 mM Tris HCl pH 8.3 (at 25° C.) and 2.5 U Taq DNA polymerase (Perkin-Elmer Cetus) in a final volume of 0.1 ml. Unless otherwise noted, all reactions were performed for 30 cycles with cycling times of 94° C. for 1.5 minutes, 60° C. for 1.5 minutes and 72° C. for 4 minutes.

All oligonucleotide primers were synthesized on an Applied Biosystems 380A DNA Synthesizer using well-known, standard cyanoethyl phosphoramidate chemistry.

The oligonucleotides have the following sequences:

| 1 | AN [SEQ ID NO: 1] | GCATGCGCGCGGCCGCGGAGGCC |
| 2 | ANpolyC [SEQ ID NO: 2] | GCATGCGCGCGGCCGCGGAGG $(C)_{14}$ |
| 3 | Flg-1 [SEQ ID NO: 3] | ACATCCAGCTGGTATGTGTG |
| 4 | Flg-2 [SEQ ID NO: 4] | TACGGTCGACCGTACTCATTCTCCACAATGCA |

| 5 | Flg-PE-165non [SEQ ID NO: 5] | GCCATTTTTCAACCAGCGC |
| 6 | Flg-PE-141non [SEQ ID NO: 6] | GGGGTTTGGGGTCCCACTGGAA |
| 7 | GT11-R1 [SEQ ID NO: 7] | TGACACCAGACCAACTGGTAATGG |
| 8 | GT11-R3 [SEQ ID NO: 8] | TAATGGTAGCGACCGGCGCTCAGC |
| 9 | 3'mbek [SEQ ID NO: 9] | TCATGTTTTAACACTGCCGTTTATGTGTGGATA |
| 10 | Bek4A [SEQ ID NO: 10] | GGAATTCAAGCTTCTAGACCACCATGGTCAGCTGGGGT CGTTTCA |
| 11 | Bek1B [SEQ ID NO: 11] | TCCTATTGTTGGGCCCCAAGTGCA |

Isolation of 5' flg clones

Flg cDNA 5' of the internal EcoRI site (5' end of pC51, Ruta, et al., 1988 supra) was obtained by anchored PCR (Loh, et al., 1989 supra) using primer Flg-1 to specifically prime first strand cDNA synthesis from 50 μg human endothelial cell total RNA. After dG tailing of the first strand with terminal deoxynucleotidyl transferase, PCR amplification (30 cycles) with primers Flg-2, AN, and 10 pmol ANpolyC was performed with cycling times of 94° C. for 1.5 minutes, 50° C. for 2 minutes and 72° C. for 4 minutes. A single PCR product was obtained which extended the C51 sequence 170 bp in the 5' direction. The new sequence was used to design the two oligonucleotides which were used with λgt$_{11}$ arm-specific oligonucleotides to amplify, by PCR, 5' flg clones contained in the endothelial cell library. The second PCR reaction was performed with 2×10$^6$ phage and the oligonucleotides Flg-PE-165non and GT11-R1. The third reaction used 5 μl of the preceding reaction as template for the oligonucleotide primers Flg-PE-141non and GT11-R3. The 560 bp product from the third reaction was made blunt ended by incubation with T4 DNA polymerase and cloned into the SmaI site of both pGem-1 (Stratagene) and M13mp19 and sequenced. The 5' flg PCR product in pGem-1 was excised, radiolabelled by random hexamer priming (Feinberg & Vogelstein, Anal. Biochem., 137: 266 (1984)), and used to rescreen the HUVEC cDNA library in order to obtain a cDNA clone free of potential PCR generated artifacts. Only one clone in 2×10$^6$ screened recombinant phage was detected. Nucleotide sequence analysis of the cDNA insert of this clone revealed that its sequence was identical to the PCR-generated product and that it terminated at the EcoRI site shared by the partial flg clone pC51. This cDNA was digested with EcoRI and SacI which cuts 50 bp 5' of the translation initiation ATG, and the 650 bp EcoRI/SacI fragment was cloned into similarly cleaved pGem-1. A full-length flg cDNA was constructed by cloning the 3' EcoRI flg insert from pC51 into the EcoRI site of this 5' flg clone. The full length cDNA was excised with SmaI/ApaI, made blunt ended with T4 DNA polymerase, and cloned into an EcoRV site of pMJ30. pMJ30 is derived by substitution of a linker containing an EcoRV cloning site for the aFGF insert in p267 (Jaye, et al., EMBO. J., 7: 963–969 (1988)).

Isolation of overlapping human bek cDNA clones

A one-day-old human brain stem cDNA library in λgt$_{11}$ (Kamholz, et al., Proc. Nat'l. Acad. Sci. USA, 83: 4962–4966 (1986)) was screened with an anti-sense 33-base oligonucleotide (3'mbek) complementary to the 3' end of the partial murine bek coding sequence (Kornbluth, et al., 1988 supra). Thirty-two positive cDNA clones were isolated from a screen of 1.5×10$^6$ recombinant plaques and the longest clone, λbek5, was chosen for further analysis. λbek5 was digested with EcoRI and the 5' 2.2 kb and the 3' 1.0 kb EcoRI fragments were subcloned separately into M13mp19 and pGem-1 vectors for further manipulations.

cDNA clones for the 5' end of human bek were isolated by screening the brainstem library a second time with a 5' proximal 750 bp fragment from λbek5. The fragment was radiolabelled by nick-translation and used to screen 1.5×10$^6$ plaques. Fifty-four hybridizing plaques were detected and one, λbek78, overlapped the original cDNA clone and extended 218 bp further in the 5' direction.

RNA Isolation and Northern Analysis

A204 (human rhabdomyosarcoma), U563 (human glioblastoma) and NTERA-2 cl.D1 (human teratocarcinoma) cells were grown in DMEM with 10% fetal calf serum. Human umbilical vein endothelial cells (HUVEC) were grown in Medium 199 containing 10% fetal calf serum, 10 U/ml heparin (Upjohn) and 5 ng/ml recombinant aFGF. Total RNA was isolated from NTERA2cl.D1 cells with guanidine HCl (Wang, et al., Dev. Biol. 107: 75–86 (1985)) and from A204, HUVEC and U563 cells with guanidine isothiocyanate (Chirgwin, et al., Biochem. 18: 5294–89 (1979)). The RNA was quantitated by its optical absorbance at 260 nm. Samples containing 4 μg total RNA were fractionated on a 1.25% agarose gel containing formaldehyde, transferred to nitrocellulose and then probed essentially as described (Seed, In: Genetic Engineering, Setlow et al., eds., Vol 4 pp 91–102, Plenum Press New York, 1982)) using probes generated by random hexamer priming (Feinberg and Vogelstein, Anal. Biochem. 137: 256 (1984)). The flg probe was a 550 bp ApaI/EcoRI fragment entirely contained within the 3' non-coding region. The bek probe was a 850 bp Tth111I/EcoRI fragment entirely contained within the 3' non-coding region.

EXAMPLE II

This example illustrates the expression of full length flg and bek in a mammalian expression vector.

As mentioned in the previous Example, the full length flg clone was excised with SmaI/AnaI, made blunt ended with T4 DNA polymerase, and cloned into an EcoRV site of expression plasmid pMJ30. pMJ30 having been derived by linker substitution for the aFGF insert in p267 (Jaye, et al., EMBO J. 7: 963–969 (1988)). Accordingly, pMJ30 containing the full length flg sequence is denoted as pflgFL24.

The human bek cDNA was prepared for mammalian expression by amplifying 276 bp fragment from λBek78 with the oligonucleotide primers Bek4A and Bek1B. After digestion with HindIII and BclI, the 5' 222 bp fragment was joined to the 2.2 kb subclone of λbek5 at a unique BclI site in the region of overlap. The PCR amplified fragment added restriction sites and a favorable translational initiation sequence immediately upstream of the putative initiator ATG codon. The 3' 1.0 kb EcoRI bek cDNA fragment was inserted subsequently. For introduction into NIH 3T3 cells, a 2.5 kb fragment containing the entire human bek coding region was subcloned into pMJ30. The nucleotide sequence of all clones was determined on both strands by chain termination (Sanger, et al., *Ann. N.Y. Acad. Sci.*, 51: 660–672 (1977)). Accordingly, pMJ30 containing full length bek sequence is denoted as pGC37.

NIH 3T3 cells were grown in Dulbecco's Modified Eagle's Medium (DMEM) with 10% calf serum. NIH 3T3 cells were transfected with calcium phosphate co-precipitates of either 1 µg pSV2neo, or 1 µg pSV2neo with 20 µg of expression vectors containing the full coding sequence of either flg cDNA or bek cDNA. It should be noted that psv2neo merely provides a selectable marker and any other equivalent co-transfectant system may be employed. Individual clones were selected in 500 µg/ml Geneticin (Gibco) and maintained in media containing 200 µg/ml Geneticin.

The coding regions of the cDNAs for bek and flg were separately inserted into a mammalian expression vector immediately downstream of the SV40 promoter and cytomegalovirus enhancer. NIH 3T3 cells were cotransfected with a 1:20 mixture of pSV2neo (Southern and Berg, *J. Mol. Appl. Gen.*, 1: 327–341 (1982)) and either a bek or flg expression vector, and transfectants were selected by growth in the presence of 500 µg/ml Geneticin (Gibco). Approximately 50 clones of each were screened for overexpression of FGF receptors by crosslinking to [$^{125}$I]aFGF. NIH 3T3 cells transfected with pSV2neo alone served as controls. Clones of both bek- and flg-transfected cells displaying increased binding for aFGF were identified in this way, indicating that bek and flg were both aFGF receptors. One bek transfected clone, Nbek8, and one flg transfected clone, Nflg26, were chosen for further analysis based on their increased expression of aFGF receptors.

The translation products of the flg and bek expression vectors were analyzed by metabolically labeling Nbek8 and Nflg26 cells with [$^{35}$S]methionine, preparing cell extracts and immunoprecipitating with bek- and flg-specific antipeptide antisera.

Peptides corresponding to the COOH terminal 15 amino acids of flg (Flg-1) or the COOH-terminal 17 amino acids of bek (Bek-1) were synthesized and coupled to keyhole limpet hemocyanin using the crosslinking reagent 1-ethyl-3-(3-dimethylaminopropyl) carbodiimide. Rabbits were then immunized with these reagents emulsified in complete Freund's adjuvant to generate the polyclonal antisera Anti Flg-1 and Anti Bek-1.

Cells at 90% confluence grown in 10 cm tissue culture dishes (Falcon) were washed with methionine-free DME and incubated for 6 hours in methionine-free DME containing 10% calf serum and 100 µCi/ml [$^{35}$S]methionine (Amersham). The cells were then washed three times with PBS (Gibco) and scraped in 0.5 ml of lysis buffer (20 mM Hepes pH 7.5, 150 mM NaCl, 10% glycerol, 1% Triton X-100, 1.5 mM MgCl$_2$, 1 mM EDTA, 1 µg/ml aprotinin, 1 µg/ml leupeptin, 1 mM phenylmethylsulfonyl fluoride) and incubated for 15 minutes on ice. The lysates were centrifuged for 15 minutes in an Eppendorf centrifuge at 4° C. Three mg of protein A-Sepharose per sample was swollen and washed with 20 mM Hepes, pH 7.5, and then mixed for 30 minutes at room temperature with the corresponding rabbit anti-peptide antiserum (Anti Flg-1 and Anti Bek-1), followed by three washes with HNTG buffer (20 mM Hepes, pH 7.5, 150 mM NaCl, 0.1% Triton X-100, 10% glycerol).

The protein A-Sepharose/antibody complexes were then incubated with the respective clarified cell lysates for 60 minutes in HNTG buffer at 4° C., washed twice with 50 mM Hepes, pH 8.0, 500 mM NaCl, 0.2% Triton X-100 and 5 mM EGTA, twice with 50 mM Hepes, pH 8.0, 150 mM NaCl, 0.1% Triton X-100, 5 mM EGTA and 0.1% SDS and finally twice with 10 mM Tris-HCl pH 8 and 0.1% Triton X-100. Laemmli sample buffer (Laemmli, *Nature* 227: 680–685 (1970)) was added to the washed immunoprecipitates which were then boiled for 4 minutes and separated on a SDS-(7%)polyacrylamide gel. Autoradiograms of the dried gels were made on Kodak X-Omat film (Eastman Kodak Co., Rochester, N.Y.).

The immunoprecipitates were subjected to SDS-PAGE followed by autoradiography (FIG. 4). A band of 150 kDa was specifically immunoprecipitated from flg-transfected cells with fla-antipeptide antiserum (lane 3) while bek-antipeptide antiserum specifically immunoprecipitated a band of 135 kDa (lane 7) from bek-transfected cells. Immunoprecipitation in the presence of the corresponding antigenic peptide completely eliminates the precipitation of flg and bek specific proteins. The deduced amino acid sequences of flg and bek predict mature core proteins of 89,437 and 89,750 daltons, respectively; glycosylation at potential sites in the extracellular domains would result in higher molecular weight forms. Treatment of NFlg26 and Bek8 cells with tunicamycin in order to block glycosylation resulted in bek and flg products of reduced molecular weights, more consistent with their predicted core protein sizes (lanes 4 and 8). The results demonstrate that both bek and flg are glycoproteins. Although the larger size of flg compared to bek is consistent with the number of potential N-linked glycosylation sites (9 vs. 8) in each, the flg product isolated from tunicamycin treated cells migrates more slowly than would be predicted from its amino acid sequence. The reason for the slower migration is not known but is probably not due to the recombinant flg construction, since flg from NFlg26 and A204 rhabdomyosarcoma cells have identical apparent molecular weights, both before and after tunicamycin treatment.

No bek or flg protein was detected in immunoprecipitates from control cells (lanes 1, 2, 5 and 6). In previous experiments, FGF-crosslinked flg protein was immunoprecipitated from NIH 3T3 2.2 cells (Ruta, et al., 1989 supra) which clearly express endogenous flg. The inability to detect flg in control experiments is due primarily to the small number of cells analyzed and the short autoradiographic exposure times permitted by the use of the bek- and flg-overexpressing cell lines.

The basal level of endogenous fibroblast growth-factor receptors will vary from cell type to cell type. 3T3 cells contain about 5–10,000 such receptors but some 3T3 subclones such as 3T3 2.2 cells may contain up to 30,000 receptors per cell. The term "over-expressing" cells as used herein refers to cells having about 50,000 receptors or more. Initial transfection of 3T3 cells with the plasmid disclosed above yield cells having about 50,000 receptor/cell. However, over time in culture clones may be selected which expression 300,000 or more receptors/cells. If DHFR-deficient CHO cells are transfected and amplified by methotrexate selection they would be expected to produce up to a million or more receptors per cell.

EXAMPLE III

Radioiodination and Binding of FGF

Bovine derived aFGF, purified as previously described (Burgess, et al., *J. Biol. Chem.*, 260: 11389–11392 (1985)), human recombinant bFGF (a kind gift of Dr. Moscatelli) and human recombinant kFGF (a kind gift of Dr. Claudio Basilico) were radioiodinated using the protocol for Enzymobeads (BioRad). The specific activity of the radiolabelled ligand was determined by radioisotope dilution using the respective unlabelled competitsr. The concentrations of the unlabelled ligands were determined by amino acid analysis (Jaye, et al., 1987 supra). The specific activity of the different preparations of [$^{125}$I]aFGF varied between 130,000–760,000 cpm/ng and the specific activity for [$^{125}$I] bFGF between 50,000–500,000 cpm/ng. The specific activity of [$^{125}$I]kFGF varied from 50,000–200,000 cpm/ng.

The binding assay was performed as follows:

Fibronectin-coated 24 well dishes containing 1×10$^5$ cells/well were placed on ice, and the wells were rinsed twice with cold binding buffer (DMEM, 1 mg/ml BSA, 5 U/ml heparin, 50 mM Hepes, pH 7.4). Dishes were incubated on ice with 1 ml of ice cold binding buffer for 20 minutes, followed by 2 hours at 4° C. with serial dilutions of the [$^{125}$I]FGF in cold binding buffer without heparin. Nonspecific binding was obtained using the same serial dilutions but in the presence of 100 fold molar excess of non-radioactive aFGF. After incubation, the cells were placed on-ice and rinsed twice with ice cold binding buffer minus heparin and then solubilized in 0.3N NaOH 37° C., 15 minutes. When [$^{125}$I]bFGF was used the cells were placed on ice after incubation, washed three times with PBS, twice with 1 ml 2M NaCl in 20 mM Hepes, pH 7.5 and twice with 1 ml 2M NaCl in 20 mM sodium acetate, pH 4.0. The radioactivity released by the acid 2M NaCl wash represents specific binding to high affinity sites (Moscatelli, *J. Cell. Physiol.*, 131: 123–130 (1987)).

Covalent Crosslinking of [$^{125}$I] Acidic FGF [$^{125}$I] Basic FGF and [$^{125}$I]kFGF to Intact Cells NFlg26, NBek8 and NNeo4 cells were grown in 60 mm tissue culture dishes coated with human fibronectin. At confluency, cells were washed twice with binding buffer (DMEM containing 0.2% BSA and 20 mM Hepes, pH 7.5) and incubated for 90 minutes at 4° C. with binding buffer containing 25 ng/ml of [$^{125}$I]aFGF, [$^{125}$I]bFGF or [$^{125}$I]kFGF. After washing once with binding buffer and once with PBS, cells were further incubated for 20 minutes at 4° C. with PBS containing 0.3 mM disuccinimidyl suberate (Pierce) as crosslinker (prepared as 30 mM stock solution in DMSO). Cells were then washed once with 10 mM Hepes, pH 7.5, 200 mM glycine, 2 mM EDTA, once with PBS and then scraped in PBS and collected by centrifugation in an Eppendorf centrifuge. Cell pellets were lysed in 100 µl of lysis buffer (20 mM Hepes, pH 7.5, 150 mM NaCl, 1% Triton X-100, 10% glycerol, 1.5 mM MgCl$_2$, 1 mM EDTA, 1 µg/ml aprotinin, 1 µg/ml leupeptin and 1 mM PMSF), incubated for 15 minutes on ice and centrifuged for 15 minutes at 4° C. in an Eppendorf centrifuge. Approximately equal volumes of the supernatants of each sample were mixed with Laemmli sample buffer (Laemmli, *Nature*, 227: 680–685 (1970)), boiled for 4 minutes and fractionated on an SDS-7% polyacrylamide gel. The gels were stained with Coomassie Brilliant Blue to verify that all samples contained approximately equal amounts of protein. Autoradiograms of the dried gels were made on Kodak X-Omat film.

Figure 5B:
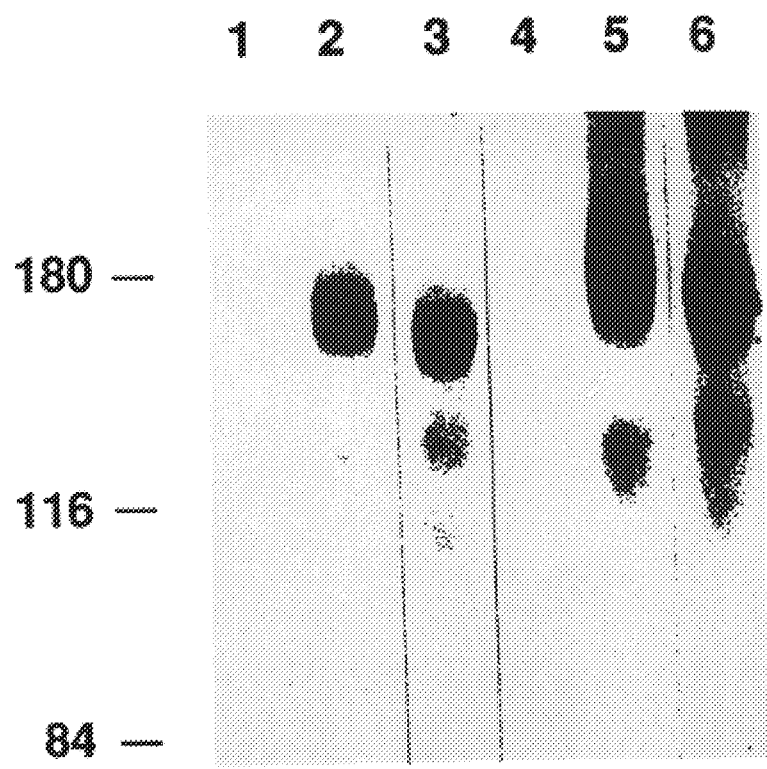

The ability to screen clones for overexpression of bek and flg by affinity crosslinking with [$^{125}$I]aFGF suggested that both bek and flg bound aFGF with high affinity. The binding of [$^{125}$I]aFGF, [$^{125}$I]bFGF and [$^{125}$I]kFGF was analyzed, in parallel, to bek- and flg-overexpressing cells. Following incubation of the cells with [$^{125}$I]aFGF, [$^{125}$I]bFGF or [$^{125}$I]kFGF receptor-FGF complexes were covalently crosslinked with disuccinimidyl suberate, solubilized, and subjected to SDS-PAGE and autoradiography (FIG. 5). A single band of 165 kDa was crosslinked to both aFGF and bFGF in flg overexpressing cell lines (lanes 2 and 5). Similarly, a single band of 150 kDa was crosslinked to both aFGF and bFGF in bek overexpressing cell lines (lanes 3 and 6). After subtraction of the molecular weight of the ligands (approximately 15 kDa) the size of the crosslinked band in the flg and bek overexpressing cell lines (150 and 135, kDa, respectively) corresponds exactly to the size of the immunoprecipitated flg and bek proteins (FIG. 4). The apparent slightly higher size of the bands when [$^{125}$I]kFGF is crosslinked (FIG. 5B) compared to those when aFGF or bFGF is crosslinked (FIG. 5A) is because of the difference in size of kFGF (22Kd) verses aFGF or bFGF (16Kd). No crosslinked product was observed in control cells, which we attribute again to the short autoradiographic exposure time afforded by the intensity of the signals obtained with the overexpressing cell lines.

Equilibrium binding analysis of flg and bek radioloabled with acidic, basic and k-fibroblast growth factors Acidic and basic FGF were radioiodinated and purified on heparin-Sepharose as described above. The dissociation constants of bek and fiq for aFGF and bFGF were established by saturation binding analysis of the overexpressing cell lines with the iodinated ligands. Binding of both aFGF and bFGF to bek and flg was specific and saturable (FIG. 6A, inserts). In addition, binding of [$^{125}$I]aFGF and [$^{125}$I] bFGF at saturation was completely eliminated in the presence of a 100 fold molar excess of either aFGF or bFGF, indicating that each ligand effectively competed with the other for binding to the same sites. Scatchard, (*Ann. N.Y. Acad. Sci.* 51: 660–672 (1949)) analysis of the binding data for a typical experiment (FIG. 6A) indicates that the flg overexpressing cells bear approximately 55,000 receptors per cell with affinities of 24 pM and 47 pM for aFGF and bFGF respectively. Likewise, the bek-overexpressing cells bear approximately 64,000 receptors per cell with affinities of 47 pM and 82 pM for aFGF and bFGF respectively. kFGF binds to flg and bek with affinities of 320 and 80 pM, respectively (FIG. 6B). Also kFGF binds to bek with similar affinity as does bFGF but binds to flg with 4-foldless avidity than does bFGF. The data from additional experiments yield apparent Kds of aFGF for flg in the range of 20–80 pM and for bek in the range of 40–100 pM. A similar variation in the Kds of bFGF binding to flg (50–150 pM) and bek (80–150 pM) is observed but within any single experiment bFGF always shows approximately 2-fold lower affinity for either flg or bek when compared to aFGF. The range of values probably arises from determinations of the specific activity and biological integrity of different preparations of the iodinated ligands. Nevertheless, the data clearly demonstrate that bek and flg bind aFGF with similar high affinities, and bind to bFGF with approximately 2-fold lower affinity than aFGF. These conclusions were supported by competition (isotope dilution) experiments in which increasing amounts of nonradioactive aFGF or bFGF competed for binding with [$^{125}$I]aFGF and [$^{125}$I]bFGF to flg- and bek-overexpressing cells.

DRUG SCREENING

The biologically active transformed cells may be used to screen compounds for their effectiveness in inhibiting the binding of FGFs to their cognant receptors. Having established the parameters of ligand/receptor interaction in the absence of potential inhibitors, it is merely a routine task to preincubate the cells with a test sample containing a compound to be evaluated, added labelled FGF and measure the reduction of FGF binding, if any.

Alternative assays are possible. For example, rather than measuring FGF binding directly, the effect of FGF (i.e. an intracellular event) may be assayed. One such event is protein phosphorylation either of the receptor itself or another intracellular target such as phospholipase C-γ. The appearance of phosphorylated protein can be measured by reactivity of such proteins with an anti-phosphotyrosine antibody.

This invention relates to useful cell lines for drug evaluation, not to any particular assay employed. As mentioned previously, it is not necessary to express the entire receptor molecule in order to provide a useful screening system. For example, it has been discovered that an extracellular domain in which the first Ig-domain and the "acidic box" have been deleted is still capable of binding FGF-ligand. As mentioned above, host cells expressing on the cytoplasmic domain may be used as a convenient source of protein kinase for the testing of candidated tryphostins. E. coli transformed with a plasmid containing only the cytoplasmic domain has been shown to be useful for this purpose. Given the intact sequence of flg and bek provided by this invention, it is a matter of routine skill to produce fragments of the various domains by means of PCR techniques or solid state peptide synthesis and to evaluate same for their ability to bind ligand or phosphorylate proteins.

Potential therapeutics include but are not limited to small organic molecules, receptor fragments themselves or antibodies that inhibit the binding of ligand to extracellular domain or effect protein kinase activity.

Compounds with inhibitory activity are potentially useful as therapeutics for the treatment of disease states characterized by undesirable FGF-mediated cellular responses. Among the diseased states that have been shown to be characterized by such responses include cancer, specifically certain forms of breast cancer, psoriasis, arthritis, atherosclerosis and benign prostatic hypertrophy.

The therapeutic agents of this invention may be administered alone or in combination with pharmaceutically acceptable carriers, the proportion of which is determined by the solubility and chemical nature of the compound, chosen route of administration and standard pharmaceutical practice. For example, they may be administered orally in the form of tablets or capsules containing such excepients as starch, milk sugar, certain types of clay and so forth. They may be administered sublingually in the form of troches or lozenges in which the active ingredient is mixed with sugar and corn syrups, flavoring agents and dyes; and then dehydrated sufficiently to make it suitable for pressing into a solid form. They may be administered orally in the form of solutions which may contain coloring and flavoring agents or they may be injected parenterally, that is, intramuscularly, intravenously or subcutaneously. For parenteral administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less then the optimum dose of the compound and increase the dosage by small increments until the optimum effect under the circumstances is reached. It will generally be found that when the composition is administered orally, larger quantities of the active agent will be required to produce the same effect as a smaller quantity given parenterally.

What is claimed is:

1. An isolated receptor protein comprising the amino acid sequence of human bek as shown in SEQ ID NO: 13, or an allelic variant thereof.

2. The receptor according to claim 1 which binds at least three heparin-binding growth factors.

3. The receptor according to claim 2 wherein said growth factors are selected from the group consisting of acidic fibroblast growth factor, basic fibroblast growth factor and k-fibroblast growth factor.

4. An isolated protein fragment comprising two immunoglobulin-like repeats of a human fibroblast growth factor receptor, said receptor comprising the amino acid sequence of human bek as shown in SEQ ID NO: 13, or an allelic variant thereof.

5. The protein fragment according to claim 4, comprising the extracellular domain of said receptor.

6. A composition comprising a protein fragment according to claim 5 and a carrier.

7. A composition comprising a protein fragment according to claim 4 and a carrier.

8. An isolated protein fragment comprising the cytoplasmic domain of a human fibroblast growth factor receptor, said receptor comprising the amino acid sequence of human bek as shown in SEQ ID NO: 13, or an allelic variant thereof.

9. A composition comprising a protein fragment according to claim 8 and a carrier.

* * * * *